US006600030B2

(12) United States Patent
Dean et al.

(10) Patent No.: US 6,600,030 B2
(45) Date of Patent: Jul. 29, 2003

(54) DELAYED PROGRESSION TO AIDS BY A MISSENSE ALLELE OF THE CCR2 GENE

(75) Inventors: Michael Dean, Frederick, MD (US); Stephen J. O'Brien, Frederick, MD (US); Michael Smith, Jefferson, MD (US); Mary Carrington, Gaithersburg, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/131,827

(22) Filed: Aug. 10, 1998

(65) Prior Publication Data

US 2002/0038469 A1 Mar. 28, 2002

Related U.S. Application Data

(60) Provisional application No. 60/055,659, filed on Aug. 14, 1997.

(51) Int. Cl.[7] ........................ A61K 38/17; A61K 48/00; C07H 21/02; C07H 21/04; C07K 14/47

(52) U.S. Cl. ....................... 536/23.5; 424/208.1; 435/6; 435/69.1; 435/70.1; 435/71.1; 435/71.2; 435/325; 435/243; 435/252.3; 435/320.1; 435/975; 514/44; 530/350; 536/23.1; 536/24.3; 536/24.31; 536/24.33

(58) Field of Search ........................... 424/208.1; 435/6, 435/69.1, 70.1, 71.1, 71.2, 325, 243, 252.3, 320.1, 975; 514/44; 530/350; 536/23.1, 23.5, 24.3, 24.31, 24.33

(56) References Cited

FOREIGN PATENT DOCUMENTS

| | | | |
|---|---|---|---|
| WO | WO 95/19436 | 7/1995 | ........... C12N/15/12 |
| WO | WO 97/31949 | 9/1997 | ........... C07K/16/28 |
| WO | WO 98/27815 | 7/1998 | .......... A01N/43/42 |

OTHER PUBLICATIONS

Liu et al. Cell, Aug. 9, 1996, vol. 86, No. 3 p. 367–377.*

Kostrikis et al. "A chemokine Receptor CCR2 Allele Delays HIV–1 Disease Progression and is Associated with a CCR5 Promoter Mutation" *Nature Medicine* 4(3):350–353, Mar., 1998.

Michael et al. "The Role of CCR5 and CCR2 Polymorphisms in HIV–1 Transmission and Disease Progression" *Nature Medicine* 3(10):1160–1162, Oct. 1997.

Smith et al. "Influence of CCR2 and CCR5 Receptor Genetic Variants on HIV–1 Infection and Disease Progression" Abstract No. 232, 47$^{th}$ Annual Meeting of the American Society of Human Genetics, Baltimore, MD, Oct. 28–Nov. 1, 1997.

Smith et al. "Contrasting Genetic Influence of CCR2 and CCR5 Varians on HIV–1 Infection and Disease Progression" *Science* 277:959–965, Aug. 15, 1997.

Frade et al. "The Amino–Terminal Domain of the CCR2 Chemokine Receptor Acts as Coreceptor for HIV–1Infection " *J. Clinical Investigation* 100(3):497–502, Aug., 1997.

Sozzani et al. "MCP–1 and CCR2 in HIV Infection: Regulation of Agonist and Receptor Expression" *J. Leukocyte Biol.* 62:30–33.

Simmons et al. "Potent Inhibition of HIV–1 Infectivity in Macrophages and Lymphocytes by a Novel CCR5 Antagonist" *Science* 276:276–279, Apr. 11, 1997.

Connor et al. "Change in Coreceptor Use Correlates with Disease Progression in HIV–1 Infected Individuals" *J. Exp. Med.* 185(4):621–628, Feb. 17, 1997.

Rucker et al. "Regions in β–Chemokine Receptors CCR5 and CCR2b that Determine HIV–1 Cofactor Specificity" *Cell* 87:437–446, Nov. 1, 1996.

Charo et al. "Molecular Cloning and Functional Expression of Two Monocyte Chemoattractant Protein 1 Receptors Reveals Alternative Splicing of the Carboxyl–Terminal Tails" *Proc.Natl. Acad. Sci. USA* 91:2752–2756, Mar. 1994.

* cited by examiner

*Primary Examiner*—Phuong T. Bui
(74) *Attorney, Agent, or Firm*—Needle & Rosenberg, P.C.

(57) ABSTRACT

The present invention relates to a CCR2 deletion mutant, designated "CCR2-64I." CCR2 is a C—C chemokine receptor and has been implicated as a co-receptor for HIV-1. It has been discovered that the presence of the CCR2-64I allele correlates with a postponement of AIDS outcomes, and that infected individuals who have the CCR2-64I allele are at a reduced risk for progression from HIV-1 infection to the development of clinical AIDS and death. Isolated nucleic acid molecule encoding CCR2-64I and the establishment of cell lines that express CCR2-64I provides valuable tools for continuing research on HIV infection. Diagnostic methods for analysis of the allelic frequency of CCR2 wild-type and 64I genes are provided. In addition, antibodies which bind to CCR2-64I, CCR2-64I variants, and CCR2 binding agents represent potential anti-HIV agents.

9 Claims, 10 Drawing Sheets

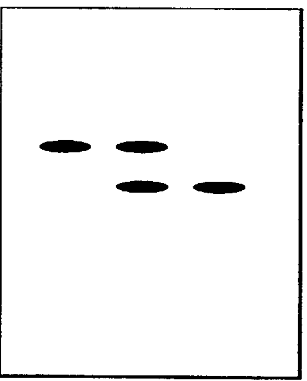

FIG. 1A

```
       1                                      33   34                                                      83
CCR2   MLSTSRSRFIRNT NESGEEVTTF FDYDYGAPCH   KFDVKQIGAQ LLPPLYSLVF IFGFVGNMLV VLILINCKKL KCLTDIYLLN
CCR5               M DYQVSSPIYD IN.YTSE..Q   .IN....A.R .......... .......... I.........R. .SM.......
CCR1           METPN TTEDYDT.YE IN.GDAT..Q   .VNERAF... .......... VI.L...I.. ..V.VQY.R. .NM.S.....
CCR3           MTTSL DTVETFG..S YYN.V.LL.E   .A.TRALM.. FV........ TV.LL..VV. .M...KYRR. RIM.N.....
CCR4      MNPTDIADT. LDESIYSNYY LYESIPKP.T   .EGI.AF.EL F......... V..LL..SV. ..V.FKY.R. RSM..V....
CXCR4      MEGIS.YTS DNYS..MGSG DYDSMKEP.F   REENANFNKI F..TI..II. LT.I...G.. I.VMGYQ... RSM..K.R.H
                                                                                64
                                                                  TM1
```

FIG. 1B

DELAYED PROGRESSION TO AIDS BY A MISSENSE ALLELE OF THE CCR2 GENE

This application claims benefit of Provisional Application No. 60/055,659, filed Aug. 14, 1997.

FIELD OF THE INVENTION

The present invention relates generally to human immunodeficiency virus and more specifically to a mutant form of an HIV co-receptor, CCR2, and its association with AIDS progression.

BACKGROUND OF THE INVENTION

Chemokines are a subgroup of immune factors that have been shown to mediate chemotactic and other pro-inflammatory phenomena (see Schall, 1991, Cytokine 3:165). The chemokines are generally short peptides. The family of chemokines or intercines, is subdivided into two distinct subfamilies, the C-X-C and C—C chemokines, according to the arrangement of the first two cysteines in their primary sequence. The members of the C—C chemokine subfamily have remarkable similarities in their structural organization and biochemical properties. These homologies are consistent with the analogies observed in their biological effects, both in vitro and in vivo. For example, RANTES, MIP-1α, and MIP-1β are all potent inducers of T-cell and mononuclear phagocyte chemotaxis, and exert diverse effects on eosinophilic and basophilic polymorphonuclear leukocytes (see Schall, op. cit.)

The C—C chemokine receptors belong to the G-protein coupled receptor superfamily 20 (see Murphy, 1994, Ann. Rev. Immunol. 12:593; Neote, 1993, Cell 72:415; Raport, 1996, J. Leukocyte Biol. 59:18). The C—C chemokine receptors consist of 7 transmembrane domains, and typically contain no introns (e.g. Federsppiel et al., 1993, Genomics 16: 707; Nomura et al., Int. Immunol. 5:1239)

It has recently been shown that the chemokines RANTES, MIP-1α, and MIP-1β, act as natural suppressors of HIV-1 infection (see Cocchi et al., 1995, Science 270:1811; Baier et al., 1995, Nature 378:563). Several groups have shown that the C—C receptor CCR5, which acts as the principal cellular receptor for RANTES, NIIP-1α, and MIP-1β is an efficient co-receptor for macrophage trophic isolates of HIV-1 (e.g. Combadiere et al., 1996, J. Leukocyte Biology 60:3362). The closely related CCR2 molecule can also act as a co-receptor for some HIV-1 strains (see Doranz et al, 1996, Cell 85:1149; Deng et al., 1996, Nature 381:661). CCR2 serves as a competent co-receptor for at least one dual trophic HIV-1 strain, but not for other M-tropic strains that utilize CCR5 (Choe, et al., 1996, Cell 85: 10 1135; Doranz et al., 1996, Cell 85:1149). The importance of such dual-tropic strains is unclear. Recently, a novel CCR5 deletion mutant, termed CCR5-Δ32 has been reported (Dean et al., Science 273: 1856-62; Samson et al., Nature 382: 722–725; Liu et al., 1996, Cell 86: 367-77). Cells from homozygous CCR5-A32 individuals are highly resistant to infections. Individuals homozygous for the CCR5-A32 gene appear to be resistant to HIV infection in spite of multiple exposures. Individuals heterozygous for CCR5-Δ32 and the normal CCR5-+ allele postponed the onset of AIDS.

The CCR5 deletion mutants, plus several HLA associations that influence exposure outcome (Kaslow et al., 1996, Nature Med. 2:405; Haynes et al., 1996, Science 271–324; Detels et al., 1996, AIDS 10:102) implicate a genetic explanation for epidemiologic heterogeneity of infection and progression, but they account for only a small proportion of exposed uninfected individuals or "long term survivors" that continue to resist AIDS-defining illness 10–15 years after HIV-1 infection. For example, nearly 80% of exposed uninfected individuals are not CCR5-Δ32 homozygotes and over 60% of long-term survivors are homozygous CCR5+/+.

SUMMARY OF THE INVENTION

The present invention is based on the discovery of a variant of the CCR2 chemokine receptor which is associated with reduced progression to AIDS in HIV-infected subjects. The invention provides nucleic acid compositions which encode the CCR2 variant chemokine receptor gene, herein referred to as CCR2-64I. Vectors and host cells for expressing CCR2-64I are also provided. The nucleic acid compositions find use in diagnostic methods for the identification of individuals having a CCR2-64I allele in order to determine the likelihood that HIV-infected individuals will progress to rapid disease progression; in diagnostic methods for the identification of individuals carrying the CCR2-64I allele in order to determine treatment regimens for patients infected with HIV; for production of the encoded variant protein for antibody production; and in anti-viral therapy. A method for treating and preventing diseases which involves the inflammatory response, such as asthma, arthritis, Crohn's disease, lupus, Grave's disease, and pulmonary disease associated with cystic fibrosis, is also provided.

One aspect of the invention features isolated substantially purified CCR2-64I polypeptide and nucleic acid molecules that encode CCR2-64I. In a particular aspect, the nucleic acid molecule is the nucleotide sequence of SEQ ID NO:19. In addition, the invention features nucleic acid sequences that hybridize under stringent conditions to SEQ ID NO:19.

The invention additionally features nucleic acid sequences encoding CCR2-64I polypeptides, oligonucleotides, fragments, portions or antisense molecules thereof, and expression vectors and host cells comprising polynucleotides that encode CCR2-64I. The present invention also relates to antibodies which bind specifically to a CCR2-64I polypeptide as opposed to wild-type CCR2; pharmaceutical compositions comprising substantially purified CCR2-64I, fragments thereof, or antagonists of CCR2-64I, in conjunction with a suitable pharmaceutical carrier, and methods for producing CCR2-64I.

It is a further object of the present invention to provide a therapeutic modality consisting of transplantation into a patient suffering from a disease characterized by HIV-1 infection, of bone marrow or umbilical cord stem cells from compatible individuals that carry the CCR2-64I allele, or transplantation of treated cells from the patient (i.e., autologous transplant).

Another object of the present invention is to provide diagnostic methods for the identification of individuals carrying the CCR2-64I allele based on the amplification of the CCR2 sequence, or hybridization to the sequence, to reflect the presence or absence of the CCR2-64I allele.

Another object of the invention is to provide a diagnostic kit for determining the CCR2 allelic profile of an individual, comprising amplification primers, hybridization probes or antibodies which recognize wild-type CCR2 and amplification primers, hybridization probes, or antibodies which recognize CCR2-64I.

A further object of the invention is to provide a method for treating or preventing in a subject having or at risk of having, a disease characterized by HIV infection, comprising administering to a patient bone marrow cells, CD34+ cells, umbilical cord cells, or CD4+ cells from an individual homozygous for CCR2-64I.

An object of the invention is to provide antibodies that bind CCR2-64I specifically, such that the antibody is suitable for use in diagnosing or treating a disease characterized by HIV infection or another inflammatory response.

In fulfilling these and other objects, there has been provided, in accordance with one aspect of the invention, a method of treating or preventing a disease characterized by HIV infection or an inflammatory response, comprising administering to a patient an agent to inactivate the CCR2 receptor. In a preferred embodiment the agent is a C—C chemokine analog, an antibody, an oligonucleotide antisense to CCR2 mRNA, or a ribozyme. In another preferred embodiment, the agent is administered ex vivo or is administered directly to the patient.

BRIEF DESCRIPTION OF THE DRAWINGS

FIG. 1A shows a SSCP gel indicating the CCR2 variant pattern.

FIG. 1B illustrates the amino acid sequence of normal CCR2 (SEQ ID NO: 13) and related human chemokine receptors, CCR5 (SEQ ID NO: 14), CCR1 (SEQ ID NO: 15), CCR3 (SEQ ID NO: 16), CCR4 (SEQ ID NO: 17) and CXCR4 (SEQ ID NO: 18). Alignment of the sequences is shown.

DESCRIPTION OF THE PREFERRED EMBODIMENTS

Definitions

Figure 2A:
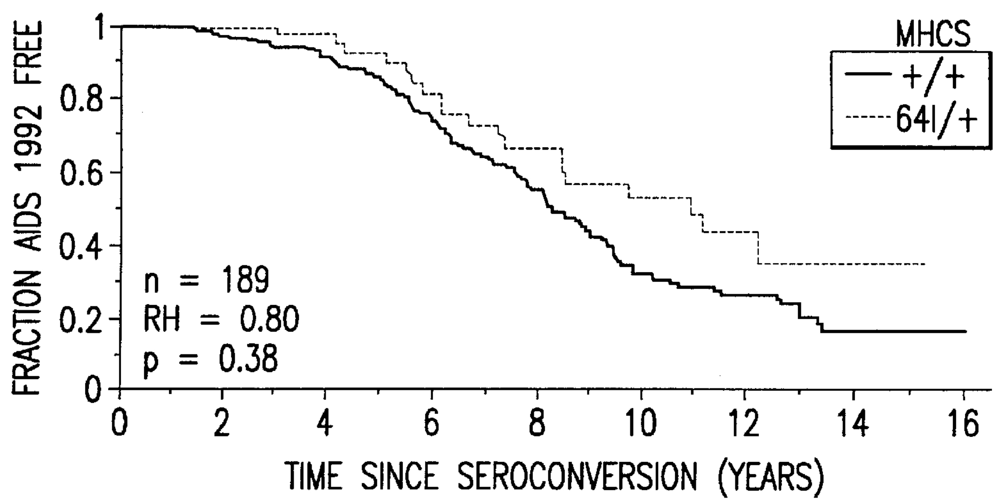
FIGS. 2A–2C show Kaplan Meier survival curves demonstrating the dependence of progression to AIDS-1992 on CCR2 genotype in MACS, HHCS and combined “All” cohort analyses.
Figure 2B:
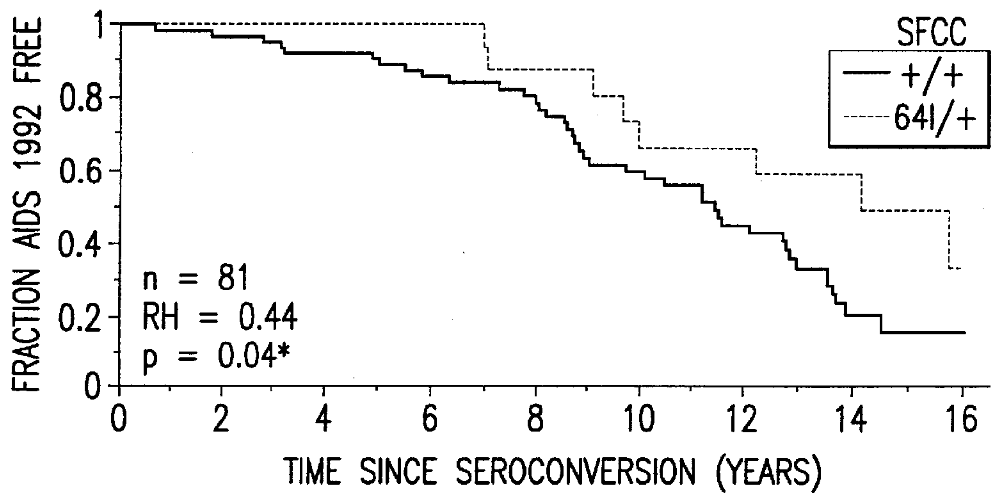
Figure 2C:
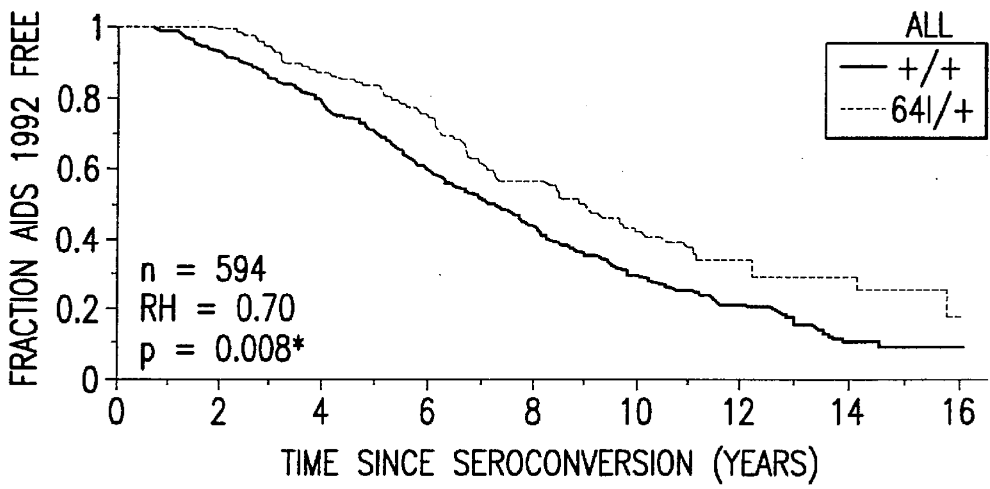

“Nucleic acid sequence” as used herein refers to an oligonucleotide, nucleotide or polynucleotide, and fragments or portions thereof, and to DNA or RNA of genomic or synthetic origin which can be single- or double-stranded, and represent the sense or antisense strand. Similarly, “amino acid sequence” as used herein refers to an oligopeptide, peptide, polypeptide, or protein sequence. Where “amino acid sequence” is recited herein to refer to an amino acid sequence of a naturally-occurring protein molecule, “amino acid sequence” and like terms (e.g., polypeptide, or protein) are not meant to limit the amino acid sequence to the complete, native amino acid sequence associated with the recited protein molecule.

A “variant” of CCR2-64I is defined as an amino acid sequence that is altered by one or more amino acids. The variant can have “conservative” changes, wherein a substituted amino acid has similar structural or chemical properties, e.g., replacement of leucine with isoleucine. More rarely, a variant can have “nonconservative” changes, e.g., replacement of a glycine with a tryptophan. Similar minor variations can also include amino acid deletions or insertions, or both. Guidance in determining which and how many amino acid residues may be substituted, inserted or deleted without abolishing biological or immunological activity can be found using computer programs well known in the art, for example, DNAStar software. A CCR2-64I variant will always have an isoleucine at position 64 of the CCR2 amino acid sequence.

A “deletion” is defined as a change in either amino acid or nucleotide sequence in which one or more amino acid or nucleotide residues, respectively, are absent.

An “insertion” or “addition” is that change in an amino acid or nucleotide sequence which has resulted in the addition of one or more amino acid or nucleotide residues, respectively, as compared to the naturally occurring CCR2-642.

A “substitution” results from the replacement of one or more amino acids or nucleotides by different amino acids or nucleotides, respectively.

As used herein, the term “’substantially purified” or “isolated” refers to molecules, either nucleic or amino acid sequences, that are removed from their natural environment, isolated or separated, and are at least 60% free, preferably 75% free, and most preferably 90% free from other components with which they are naturally associated.

“Stringency” typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term “hybridization” as used herein shall include “any process by which a strand of nucleic acid joins with a complementary strand through base pairing” (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

The term “allele” means a single form (sequence) of a gene which can present in more than one form (more than one different sequence) in a genome.

The term “wild type,” also indicated by “wt” or “+”, is the naturally occurring form of a gene without any deletions or substitutions in the DNA sequence.

“CCR2-64I” is a CCR2 gene sequence which has a nucleotide substitution (a G to A substitution) at position 190 (counting from the ATG start codon) such that the valine found at position 64 in the wild-type CCR2 amino acid sequence is replaced by an isoleucine.

“Homozygous” is defined as two of the same alleles for a given gene. According to the present invention, the CCR2 gene (wt or CCR2-64I), like most eukaryotic genes, at a frequency of two copies per genome. If both copies are genetically the same, in regard to the absence or presence of G at position 190, the individual is homozygous, i.e. s/he is either wt/wt or CCR-264I/CCR2-64I.

“Heterozygous” is defined as two different alleles being present in the genome for a given gene. According to the present invention, if one copy each of the wt and the CCR2-64I are present in the genome, the individual is heterozygous.

The term “allelic profile” means a determination of the composition of an individuals genome in regard to the presence or absence, and the copy number of the CCR2-64I allele.

As used herein, “antigenic amino acid sequence” means an amino acid sequence that, either alone or in association with a carrier molecule, can elicit an antibody response in a mammal.

As used in the present invention, the term "antibody" includes in addition to conventional antibodies, such protein fragments that have the ability to recognize and specifically and bind the CCR2 or the CCR2-64I protein.

The term "recombinant expression vector" refers to a plasmid, virus or other vehicle known in the art that has been manipulated by insertion or incorporation of the CCR5 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Overview

A key aspect of the present invention relates to the observation of a substitution allele in the first transmembrane region of the CCR2 gene found at high frequency (10-15%) among Caucasian and African Americans. Allele and genotype association analysis of patients enrolled in long-term prospective AIDS epidemiologic cohorts did not reveal an influence of CCR2-64I on HIV-1 infection. However, HIV-1 individuals carrying the CCR2-64I allele postpone the progression to AIDS 24 years longer than individuals homozygous for the wild-type allele. The implication is that the presence of CCR2-64I influences the progression of the disease. The CCR2 alleles are tightly linked to and in strong linkage disequilibrium with CCR5 alleles, one of which, CCR5-A32, also delays AIDS onset. Since mutant alleles for the two genes reside of different haplotypes their protective effects are independent and additive. In combination the effects of CCR2 and CCR5 mutant alleles account for 32-57% of long term survivors of HIV infection.

CCR2 is a recently identified chemokine receptor which can function as an HIV coreceptor (see Samson, M., et al., 1996, Genomics 36:522; Choe, H., et al, 1996, Cell 85:1135; Doranz, B. J, et al., 1996, Cell 85:1149; Charo et al., 1994, J. Biol. Chem. 91:2752; and Yamagami et al., 1994, BBRC 202:1156; all of which are incorporated herein by reference). An observation which is critical for this invention, is that homozygous CCR2-64I individuals do not display clinical deficiencies. This observation indicates that, if the level of CCR2 is reduced or if the receptor is inactivated, HIV infection can be controlled and the progress of a disease characterized by HIV infection can be reduced, without clinical drawbacks. The reduction in the level of CCR2 can further be combined with CCR5, in order to enhance the effect of the control of HIV.

Thus, the present invention focuses on treatment methodologies aimed at suppressing CCR2 gene expression or inactivating the receptor in a patient. For example, CCR2 may be inactivated by use of antibodies, or CCR2 can be blocked by the use of a modified ligand, such as a C—C chemokine analog, or CCR2 gene expression level may be reduced by antisense technology.

Furthermore, the aforementioned observations indicate a straightforward relationship between the CCR2 profile of an individual and disease characterized by HIV infection, namely, a individual carrying a CCR2-64I allele reduces progression to AIDS by 2–4 years as compared to individuals homozygous for the normal CCR2 allele. Therefore, determination of the CCR2 allelic state of an individual has important implications for the choices of preventative measures, treatments, or administration of additional or alternative diagnostic tests.

Determination of the CCR2 allelic profile of an individual can be achieved, for example, by use of antibodies to detect wild-type and 64I allele receptors; by use of nucleic acids based technology such as Polymerase Chain Reaction (PCR), wherein certain primers will detect the mutant allele; or by hybridization of a nucleic acid probe under stringent conditions, which can be coupled with restriction analysis.

A variety of functional tests are available to determine the effectiveness of any therapeutic agent according to the invention. For example, tests can be performed with tissue culture cells. They include tests to assay receptor availability, i.e. total binding to cells, or competition assays, between any therapeutic agent according to the invention, and labeled C—C chemokines. Recombinant and radiolabeled C—C chemokine MIP-1α and MIP-1β, and RANTES are commercially available, for example from Sigma Immunochemicals (St. Louis, Mo.), R&D Systems (Minneapolis, Minn.) and PEPRO (Rocky Hill, N.J.). The chemokines are known to cause chemotaxis of human peripheral monocytes. Thus another functional test comprises observation of chemotaxis in the presence of a therapeutic agent chemokine. For a further description of binding assay, chemotaxis determination and related assays, see Xu et al, 1995, Eur. J. Immunol. 25:2612-7, the contents of which are incorporated herein by reference. Yet other tests for the effectiveness of the treatment in tissue culture are known by one skilled in the art. For example, expression of viral functions or proteins can be monitored in cultured cells.

Isolation of cDNA Encoding CCR2-64I

The gene for the chemokine receptor of the present invention can be cloned from a human cDNA library. Methods used to clone novel chemokine receptor-like cDNAs from ag t11 cDNA library made from peripheral blood mononuclear cells of a patient with 25 eosinophilic leukemia have been described by Combadiere et al., *DNA Cell Biol.* 14: 673-80 (1995), which is herein incorporated in its entirety by reference.

The above-described methods can be used to identify sequences that code for one or more CCR2-64I nucleic acid sequences. It should be noted that all of the CCR2-64I variants will contain DNA sequences which encode an isoleucine at position 64 of the corresponding amino acid SEQ ID NO:19 of the present invention. But many other related sequences that code for CCR2-64I are contemplated in context of the various embodiments enumerated herein.

The invention provides an isolated polynucleotide sequence (e.g, SEQ ID NO:19) encoding a polypeptide having an amino acid sequence as set forth in SEQ ID NO:20. Nucleic acid sequences of the invention include DNA, cDNA and RNA sequences which encode CCR2-64I. It is understood that all polynucleotides encoding all or a portion of CCR2-64I are also included herein, as long as they encode a polypeptide with which contains an isoleucine at post 64 of the amino acid sequence. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, CCR2-64I polynucleotide may be subjected to site-directed mutagenesis. The polynucleotide sequence for CCR2-64I also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of CCR2-64I polypeptide encoded by the nucleotide sequence is functionally unchanged.

The polynucleotide encoding CCR2-64I includes the nucleotide sequence encoding 64I, as well as nucleic acid sequences complementary to that sequence. A complementary sequence may include an antisense nucleotide. Also included in the invention are fragments (portions) of the above-described nucleic acid sequences that are at least 15 bases in length, which is sufficient to permit the fragment to selectively hybridize to DNA that encodes the CCR2-64I. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42° C. (moderate stringency conditions); and 0.1× SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Preferably the CCR2-64I polynucleotide of the invention is derived from a mammalian organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981). Alternatively, a subtractive library, as illustrated herein is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid-or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gtl 1, can be screened indirectly for CCR2 and CCR2-64I peptides having at least one epitope, using specific antibodies. Such antibodies can be either polyclonally or monoclonally derived and used to detect expression product indicative of the presence of CCR2 cDNA (see below).

Alterations in CCR2-64I nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

DNA sequences encoding CCR2-64I can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the CCR2-64I polynucleotide sequences may be inserted into a recombinant expression vector. The term "recombinant expression vector" refers to a plasmid, virus or other vehicle known in the art that has been manipulated by insertion or incorporation of the CCR2-64I genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding CCR2-64I can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the CCR2-64I coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual. Cold Spring Harbor Laboratory, N.Y.)

A variety of host-expression vector systems may be utilized to express the CCR2-64I coding sequence. These include but are not limited to microorganisms such as bacteria transformed with recombinant bacteriophage DNA, plasmid DNA or cosmid DNA expression vectors containing the CCR2-64I coding sequence; yeast transformed with recombinant yeast expression vectors containing the CCR2-64I coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CCR2-64I coding sequence; insect cell systems infected with recombinant virus expression vectors (e.g., baculovirus) containing the CCR2-64I coding sequence; or animal cell systems infected with recombinant virus expression vectors (e.g., retrovinuses, adenovirus, vaccinia virus) containing the CCR2-64I coding sequence, or transformed animal cell systems engineered for stable expression.-Both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516-544). For example, when cloning in bacterial systems, inducible promoters such as pL of bacteriophage (plac, ptrp, ptac (ptrp-lac hybrid promoter)) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted CCR2-64I coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 1.11, A Practical Approach, Ed. D M Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, plasma membrane insertion of the gene product may be used as host cells for the expression of CCR2-64I.

Mammalian cell systems which utilize recombinant viruses or viral elements to direct expression may be engineered. For example, when using adenovirus expression vectors, the CCR2-64I coding sequence may be ligated to an adenovirus transcription/translation control complex, e.g., the late promoter and tripartite leader sequence. Alternatively, the vaccinia virus 7.5K promoter may be used. (e.g., see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the CCR2-64I gene in host cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the CCR2-64I cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, *Proc. Natl. Acad. Sci. USA* 48: 2026), and adenine phosphoribosyltransferase (Lowy, et al., 1980, Cell 22: 817) genes can be employed in tk-, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, *Proc. Natl. Acad. Sci. USA* 78: 1527); gpt, which confers resistance to mycophenolic acid (Mulligan & Berg, 1981, *Proc. Natl. Acad. Sci. USA* 78: 2072; neo, which confers resistance to the aminoglycoside G-418 (Colberre-Garapin, et al., 1981, *J. Mol. Biol.* 150: 1); and hygro, which confers resistance to hygromycin (Santerre, et al., 1984, *Gene* 30: 147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad Sci. USA* 85: 8047); and ODC (ornithine decarboxylase) which confers resistance to the ornithine decarboxylase inhibitor, 2-(difluoromethyl)-DL-omithine, DFMO (McConlogue L., 1987, In: Current Communications in Molecular Biology, Cold Spring Harbor Laboratory ed.).

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transformed with DNA sequences encoding the CCR2-64I of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Cell Lines

In one embodiment, the present invention relates to stable recombinant cell lines, the cells of which express CCR2-64I polypeptide, or coexpress human CD4 and contains DNA that encodes CCR2-64I, or coexpresses CD4 and CCR5 and contains DNA that encodes CCR2-64I. Suitable cell types include but are not limited to cells of the following types: NIH 3T3 (Murine), Mv 1 lu (Mink), BS-C-I (African Green Monkey) and human embryonic kidney (HEK) 293 cells. Such cells are described, for example, in the Cell Line Catalog of the American Type Culture Collection (ATCC). These cells can be stably transformed by a method known to the skilled artisan. See, for example, Ausubel et al., *Introduction of DNA Into Mammalian Cells*, in CURRENT PROTOCOLS IN MOLECULAR BIOLOGY, sections 9.5.1–9.5.6 (John Wiley & Sons, Inc. 1995). "Stable" transformation in the context of the invention means that the cells are immortal to the extent of having gone through at least 50 divisions.

CCR2-64I can be expressed using inducible or constitutive regulatory elements for such expression. Commonly used constitutive or inducible promoters, for example, are known in the art. The desired protein encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the desired molecule may occur through the transient expression of the introduced sequence. Alternatively, permanent expression may occur through the integration of the introduced sequence into the host chromosome. Therefore the cells can be transformed stably or transiently.

An example of a vector that may be employed is one which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors include vaccinia virus expression vectors. A third class of vectors relies upon the integration of the desired gene sequences into the host chromosome. Cells which have stably integrated the introduced DNA into their chromosomes may be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., Mol. Cell. Biol., 3:280 (1983), and others.

Once the vector or DNA sequence containing the construct has been prepared for expression, the DNA construct may be introduced (transformed) into an appropriate host. Various techniques may be employed, such as protoplast fusion, calcium phosphate precipitation, electroporation or other conventional techniques.

Use of Antibodies as Therapeutic or Diagnostic Agents

The mutation found in CCR2-64I occurs in the first transmembrane region of the CCR2 protein. This transmembrane region is completely conserved in amino acid sequence with CCR5, suggesting functional constraints on mutational variation. The mutant CCR2-64I protective allele actually has a transmembrane sequence that is identical to the CCR5 normal (or sensitive) allele. The seemingly modest changes which affect HIV outcome may do so by altering the efficiency of HIV co-receptor utilization. It follows that an antibody (Ab) or a fragment thereof, when bound to the wt sequence equivalent to the sequence found in CCR2-64I, would affect the functionality of the receptor. Such an antibody would be a useful therapeutic agent. An antibody directed to an epitope on the transmembrane region would be a preferred method of therapy. Generally, any CCR2 wt-specific antibody, is a therapeutic agent according to the invention.

Antibodies or fragments thereof are useful also as a diagnostic tool. Since the mutation of CCR2-64I is in the transmembrane region and is not exposed to the cell surface, it is desirable to open up cells such that their cellular content would be exposed. In a preferred embodiment, therefore, blood samples are obtained from an individual and treated to disrupt cell membrane. Treatment can be mechanic (cell pressure, for example) or chemical (organic agents or osmosis, for example) or enzymatic. A limited purification of the crude extract may be desirable. The methods are well known to one skilled in the art. Technical references are readily available. See, for example PROTEIN PURIFICATION—PRINCIPLES AND PRACTICE, Springer Verlag publ., New-York; and PROTEIN BIOTECHNOLOGY, Humana Press, Totowa, N.J.

According to another embodiment of the invention, anti-wt CCR2 specific monoclonal antibodies and anti-CCR2-64I specific monoclonal antibodies serve to identify the CCR2 receptor allelic profile of an individual. According to the embodiment, antibodies are produced and labeled as described below. Protein extracts from a patient are exposed separately to each of the two types of monoclonals. The results would indicate if the patient is homozygous wt/wt or (64L/64D, which of the alleles is present, as well as the heterozygous condition (wt/64I). For example, if in separate testing of aliquots of an extract employing anti-wt or anti-CCR-2-64I, both antibodies indicate presence of substrate, the heterozygote allelic condition is identified.

Preparation of Antibodies

Preparation of an antibody requires a purified moiety that can provide an antigenic determinant. For example, in the present invention, the gene sequence of the receptor and of the deletion allele are known. Regions of the gene that differ at the protein level are well defined. A protein can be raised by expression of the wt gene or of the CCR2-64I gene, or, preferably, fractions therefore. For example, the nucleic acid sequence can be cloned into expression vectors (see above). According to this embodiment, the sequence of interest is first obtained by employing PCR, or from a synthetic gene construction with overlapping and ligated synthetic oligonucleotides. Another alternative would involve synthesis of a short peptide. All those methodologies are well known to one skilled in the art. See, for example, Ausubel et al., CURRENT PROTOCOLS IN MOLECULAR BIOLOGY, Volumes 1 and 2 (1987), with supplements, and Maniatis et al., MOLECULAR CLONING, A LABORATORY MANUAL, cold Spring Harbor Laboratory.

The genetic sequence discussed above then is expressed in any known, commercially available systems. Vectors for subcloning the sequence of interest, and subsequent expression into bacterial, yeast, baculovirus, insect, or tissue culture are well known to one skilled in the art (see above). The subcloning process could, according to one embodiment, produce a fused protein with a short N- or C-terminal extension to facilitate subsequent purifications on columns or by use of antibodies. Alternatively, the protein of interest is purified by standard protein purification protocols. See for example PROTEIN PURIFICATION—PRINCIPLES AND PRACTICE, Springer Verlag publ., New York; and PROTEIN BIOTECHNOLOGY, Humana Press, Totowa N.J.

The preparation of polyclonal antibodies is well-known to those skilled in the art. See, for example, Green et al., Production of polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992), which are hereby incorporated by reference. The preparation of monoclonal antibodies likewise is conventional. See, for example, Hohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.9.3; Barnes et al., Purification of Immunoglobulin G (IgG), in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies of the present invention may also be derived from subhuman primate antibody. General techniques for raising therapeutically useful antibodies in baboons may be found, for example, in Goldenberg et al., International Patent Publication WO 91/11465 (1991) and Losman et al., *Int. J. Cancer* 46:310 (1990), which are hereby incorporated by reference.

Alternatively, a therapeutically or diagnostically useful anti-CCR2 or CCR2-64I antibody may be derived from a "humranized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86: 3833 (1989), which is hereby incorporate din its entirety by reference. Techniques for producing humanized monoclonal antibodies are described, for example, by Jones et al, *Nature* 321: 522 (1986); Riechmann et al., *Nature* 332: 323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Sin2er et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Inmunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be sued to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6: 579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoff et al., *Arch. Biochem. Biophys.* 89: 230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242:423–426 (1988); Ladner et al., U.S. Pat. No. 4,946,778; Pack et al., *Bio/Technology* 11: 1271-77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2:106.

According to the present invention antibodies or fragments thereof will be labeled and used in detection of CCR2 or CCR2-64I from protein extracts, in order to establish the allelic profile of an individual. In another embodiment, antibodies which specifically bind to CCR5Δ32, but not wild-type CCR5 and vice versa are also employed in such methods. The labeling of antibodies is well known in the art and includes, for example, incorporation of biotin or radioisotope containing amino acids. The antibody is then used in standard assays, such as, for example, Elisa assays, or detection of protein pre-separated by gel electrophoresis (Western blots). Labeling and the use of antibodies in a variety of assays are well known to the skilled artisan. Technical references include, for example Immunochemical Protocols in METH. MOLEC. BIOL., v 10, Humana Press, Totowa, N.J.; and RADIOIMMUNOASSAY OF BIOL. ACTIVE COMP.; Prentice-Hall, Inc., Englewood Cliff, N.J.

C—C Chemokine and other CCR2 Ligands

It was shown that CCR2 is a co-receptor for MIP-1α, MIP-1β, and RANTES. Given that a functional CCR2 receptor does not appear essential, any ligand which blocks CCR2 will be a useful therapeutic agent according to the invention. A ligand can be distinguished by a rational process or extensive searches of compounds can be undertaken, looking for a compound that can block the CCR2 receptor, by criteria of one or more of the above described functional tests.

A "variant" is any molecule derived from one of the ligands. This would include also peptides, or full length protein, that contains substitutions, deletions, or insertions into the protein backbone, that would still leave a 70% homology to the original protein over the corresponding portion. A yet greater degree of departure from homology is allowed if like-amino acids ("aa"), i.e. conservative aa substitutions do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of aa. For a variety of purposes, such as increased stability, solubility, or configuration concerns, one skilled in the art will recognize the need to introduce, (by deletion, replacement, or addition) other modifications. Examples of such other modifications include incorporation of rare aa, dextra-aa, glycosylation sites, cytosine for specific disulfide bridge formation, for example of possible modifications. The modified peptides can be chemical synthesized, or the isolated gene can be site-directed mutagenized, or a synthetic gene can be synthesized and expressed in bacteria, yeast, baculovirus, tissue culture and so on.

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular variant can easily be made by one skilled in the art based on practical considerations: size of the desired peptide, availability and cost of starting materials, etc. All the technologies involved are well established and well known in the art. See, for example, Ausubel et al., CURRENT PROTOCOLS 1N MOLECULAR BIOLOGY, Volumes 1 and 2 (1987), with supplements, and Maniatis et al., MOLECULAR CLONING, A LABORATORY MANUAL, Cold Spring Harbor Laboratory (1989). Yet other technical references are known and easiiy accessible to one skilled in the art.

Drug Discovery

The CCR2 receptor is also suitable as a target for various drug discovery techniques. For example, one may employ a bacteriophage library, as described by J. J. Devlin et al., *Science* (1990) 249:404-06. Briefly, a phage library is prepared by cloning a variety of peptides into the external portion of a phage coat protein, typically pIII or pVIII. The library may be amplified in a suitable bacterial host, for example *E. coli*, and is then screened for binding to the target. Phage having an insert that specifically binds to the target are isolated and amplified, and their DNA sequenced to determine the sequence of the binding peptide. In the present case, one may use either entirely random inserts (e.g., DNA having every possible sequence), or may have inserts based on a known structure. For example, one may prepare a phage library having an insert based on the consensus cytokine sequence. Such an insert may have a sequence that retains portions of sequence that are conserved across several cytokines, and have variable portions elsewhere.

One may also employ CCR2 as a target for small molecule drug discovery, by providing a library of candidate compounds and determining which compounds bind specifically to CCR2 with high affinity. Libraries of compounds may be obtained as fermentation broths, supernatants of mixed microorganism cultures, synthetic combinatorial libraries, and the like. One may provide CCR2 in functional cells and assay the alteration in activity provoked by library compounds. Alternatively one may provide CCR2 immobilized on a surface, contact the CCR2 with the library compounds, and fractionate the library by elution.

Antisense or Ribozyme Inhibition of CCR2

Antisense technology offers a very specific and potent means of inhibiting HIV infection of cells that contain CCR2, for example, by decreasing the amount of CCR2 expression in a cell. Antisense polynucleotides in context of the present invention includes both short sequences of DNA known as oligonucleotides of usually 10–50 bases in length as well as longer sequences of DNA that may exceed the length of the CCR2 gene sequence itself. Antisense polynucleotides useful for the present invention are complementary to specific regions of a corresponding target mRNA. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al, Cancer Research 48:2659 (1988). An antisense polynucleotide can be introduced to a cell by introducing a DNA segment that codes for the polynucleotide into the cell such that the polynucleotide is made inside the cell. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10-to 15-mers, while offering higher cell penetration, have lower gene specificity. In contrast, while longer polynucleotides of 20–30 bases offer better specificity, they show decreased uptake kinetics into cells. See Stein et al., PHOSPHOROTHIOATE OLIGODEOXYNUCLEOTIDE ANALOGUES in "Oligodeoxynucleotides-Antisense Inhibitors of Gene Expression" Cohen, ed. McMillan Press, London (1988). Accessibility to mRNA target sequences also is of importance and, therefore, loop-forming regions in targeted mRNAs offer promising targets. In this disclosure the term "polynucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such polynucleotides may be prepared by methods well-known in the art, for instance using commercially available machines and reagents available from Perkin-Elmer/Applied Biosystems (Foster City, Calif.).

Phosphodiester-linked polynucleotides are particularly susceptible to the action of nucleases in serum or inside cells, and therefore in a preferred embodiment the polynucleotides of the present invention are phosphorothioate or methyl phosphonate-linked analogues, which have been shown to be nuclease-resistant. Persons of ordinary skill in this art will be able to select other linkages for use in the invention. These modifications also may be designed to improve the cellular uptake and stability of the polynucleotides.

In another embodiment of the invention, the antisense polynucleotide is an RNA molecule produced by introducing an expression construct into the target cell. The RNA molecule thus produced is chosen to have the capability to hybridize to CCR2 mRNA. Such molecules that have this capability can inhibit translation of the CCR2 mRNA and thereby inhibit the ability of HIV to infect cells that contain the RNA molecule.

The polynucleotides which have the capability to hybridize with mRNA targets can inhibit expression of corresponding gene products by multiple mechanisms. In "translation arrest," the interaction of polynucleotides with target mRNA blocks the action of the ribosomal complex and, hence, prevents translation of the messenger RNA into protein. Haeuptle et al., *Nucl. Acids. Res.* 14:1427 (1986). In the case of phosphodiester or phosphorothioate DNA polynucleotides, intracellular RNase H can digest the targeted RNA sequence once it has hybridized to the DNA oligomer. Walder and Walder, *Proc. Natl. Acad Sci. USA* 85:5011 (1988). As a further mechanism of action, in "transcription arrest" it appears that some polynucleotides can form "triplex," or triple-helical structures with double stranded genomic DNA containing the gene of interest, thus interfering with transcription by RNA polymerase. Giovannangeli et al., *Proc. Natl. Acad. Sci.* 90:10013 (1993); Ebbinghaus et al. *J. Clin. Invest.* 92:2433 (1993).

In one preferred embodiment, CCR2 polynucleotides are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See Sambrook et al., *MOLECULAR CLONING: A Laboratory Manual*, Vol. 2, Chapter 11, Cold Spring Harbor Laboratory Press, Cold Spring Harbor, N.Y. (1989).

Alternatively, a CCR2 polynucleotide in the form of antisense RNA may be introduced to a cell by its expression within the cell from a standard DNA expression vector. CCR2 DNA antisense sequences can be cloned from standard plasmids into expression vectors, which expression vectors have characteristics permitting higher levels of, or more efficient expression of the resident polynucleotides. At a minimum, these constructs require a prokaryotic or eukaryotic promoter sequence which initiates transcription of the inserted DNA sequences. A preferred expression vector is one where the expression is inducible to high levels. This is accomplished by the addition of a regulatory region which provides increased transcription of downstream sequences in the appropriate host cell. See Sambrook et al., Vol. 3, Chapter 16 (1989).

For example, CCR2 antisense expression vectors can be constructed using the polymerase chain reaction (PCR) to amplify appropriate fragments from single-stranded cDNA of a plasmid such as pRc in which CCR2 cDNA has been incorporated. Fang et al., *J. Biol. Chem.* 267 25889–25897 (1992). Polynucleotide synthesis and purification techniques are described in Sambrook et al. and Ausubel et al. (eds.), CURRENT PROTOCOLS IN MOLECULAR BIOLOGY (Wiley Interscience 1987) (hereafter "Ausubel"), respectively. The PCR procedure is performed via well-known methodology. See, for example, Ausubel, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and Invitrogen (San Diego, Calif.).

The products of PCR are subcloned into cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Suitable cloning vectors are described by Sambrook et al., Ausubel, and Brown (ed.), MOLECULAR BIOLOGY LABFAX (Academic Press 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Preferably, the PCR products are ligated into a "TA" cloning vector. Methods for generating PCR products with a thymidine or adenine overhang are well-known to those of skill in the art. See, for example, Ausubel at pages 15.7.1–15.7.6. Moreover, kits for performing TA cloning can be purchased from companies such as Invitrogen (San Diego, Calif.).

Cloned antisense fragments are amplified by transforming competent bacterial cells with a cloning vector and growing the bacterial host cells in the presence of the appropriate antibiotic. See, for example, Sambrook et al., and Ausubel. PCR is then used to screen bacterial host cells for CCR2 antisense orientation clones. The use of PCR for bacterial host cells is described, for example, by Hofmann et al., "Sequencing DNA Amplified Directly from a Bacterial Colony," in PCR PROTOCOLS: METHODS AND APPLICATIONS, White (ed.), pages 205–210 (Humana Press 1993), and by Cooper et al., "PCR-Based Full-Length cDNA Cloning Utilizing the Universal-Adaptor/Specific DOS Primer-Pair Strategy," Id. at pages 305–316.

Cloned antisense fragments are cleaved from the cloning vector and inserted into an expression vector. For example, HindIII and XbaI can be used to cleave the antisense fragment from TA cloning vector pCR™-II (Invitrogen; San Diego, Calif.). Suitable expression vectors typically contain (1) prokaryotic DNA elements coding for a bacterial origin of replication and an antibiotic resistance marker to provide for the amplification and selection of the expression vector in a bacterial host; (2) DNA elements that control initiation of transcription, such as a promoter; and (3) DNA elements that control the processing of transcripts, such as a transcription termination/polyadenylation sequence.

For a mammalian host, the transcriptional and translational regulatory signals preferably are derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl Genet.* 1: 273 (1982)); the TK promoter of Herpes virus (McKnight, *Cell* 31: 355 (1982)); the SV40 early promoter (Benoist et al., *Nature* 290: 304 (1981); the Rous sarcoma virus promoter (Gorman et al., *Proc. Nat'l Acad. Sci. USA* 79: 6777 (1982)); and the cytomegalovirus promoter (Foecking et al., *Gene* 45: 101 (1980)).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell Biol.* 10: 4529 (1990); Kaufman et al., *Nucl. Acids Res.* 19: 4485 (1991).

A vector for introducing at least one antisense polynucleotide into a cell by expression from a DNA is the vector pRc/CMV (Invitrogen (San Diego, Calif.), which provides a high level of constitutive transcription from mammalian enhancer-promoter sequences. Cloned CCR2 antisense vectors are amplified in bacterial host cells, isolated from the cells, and analyzed as described above.

Another possible method by which antisense sequences may be exploited is via gene therapy. Virus-like vectors, usually derived from retroviruses, may prove useful as vehicles for the importation and expression of antisense constructs in human cells. Generally, such vectors are non-replicative in vivo, precluding any unintended infection of non-target cells. In such cases, helper cell lines are provided which supply the missing replicative functions in vitro, thereby permitting amplification and packaging of the antisense vector. A further precaution against accidental infection of non-target cells involves the use of target cell-specific regulatory sequences. When under the control of such sequences, antisense constructs would not be expressed in normal tissues.

Two prior studies have explored the feasibility of using antisense polynucleotides to inhibit the expression of a heparin binding growth factor. Kouhara et al., *Oncogene* 9: 455–462 (1994); Morrison, *J. Biol. Chem.* 266: 728 (1991). Kouhara et al. showed that androgen-dependent growth of mouse mammary carcinoma cells (SC-3) is mediated through induction of androgen-induced, heparin binding growth factor (AIGF). An antisense 15-mer corresponding to the translation initiation site of AIGF was measured for its ability to interfere with androgen-induction of SC-3 cells. At concentrations of 5 μM, the antisense polynucleotide effectively inhibited androgen-induced DNA synthesis. Morrison showed that antisense polynucleotides targeted against basic fibroblast growth factor can inhibit growth of astrocytes in culture. Thus, the general feasibility of targeting an individual gene product in a mammalian cell has been established.

Antisense polynucleotides according to the present invention are derived from any portion of the open reading frame of the CCR2 cDNA. Preferably, mRNA sequences (1) surrounding the translation initiation site and (ii) forming loop structures are targeted. Based upon the size of the human genome, statistical studies show that a DNA segment approximately 14–15 base pairs long will have a unique sequence in the genome. To ensure specificity of targeting CCR2 RNA, therefore, it is preferred that the antisense polynucleotides are at least 15 nucleotides in length.

Not every antisense polynucleotide will provide a sufficient degree of inhibition or a sufficient level of specificity for the CCR2 target. Thus, it will be necessary to screen polynucleotides to determine which have the proper antisense characteristics.

Administration of an antisense polynucleotide to a subject, either as a naked, synthetic polynucleotide or as part of an expression vector, can be effected via any common route (oral, nasal, buccal, rectal, vaginal, or topical), or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain polynucleotide and about 10 mg of human serum albumin per milliliter of a phosphate buffer containing NaCl.

As much as 700 milligrams of antisense polynucleotide has been administered intravenously to a patient over a course of 10 days (i.e., 0.05 mg/kg/hour) without signs of toxicity. Sterling, "Systemic Antisense Treatment Reported," *Genetic Engineering News* 12: 1,28(1992).

Other pharmaceutically acceptable excipients include non-aqueous or aqueous solutions and non-toxic compositions including salts, preservatives, buffers and the like. Examples of non-aqueous solutions are propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. A preferred pharmaceutical composition for topical administration is a dermal cream or transdermal patch.

Antisense polynucleotides or their expression vectors may be administered by injection as an oily suspension. Suitable lipophilic solvents or vehicles include fatty oils, such as sesame oil, or synthetic fatty acid esters, such as ethyl oleate or triglycerides. Moreover, antisense polynucleotides or vectors may be combined with a lipophilic carrier such as any one of a number of sterols including cholesterol, cholate and deoxycholic acid. A preferred sterol is cholesterol. Aqueous injection suspensions may contain substances which increase the viscosity of the suspension include, for example, sodium carboxymethyl cellulose, sorbitol, and/or dextran. Optionally, the suspension also contains stabilizers.

An alternative formulation for the administration of antisense CCR2 polynucleotides involves liposomes. Liposome encapsulation provides an alternative formulation for the administration of antisense CCR2 polynucleotides and expression vectors. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., *American J. Hosp. Pharm.* 46: 1576 (1989). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N. Y Acad. Sci.* 446: 368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid-or polyethylene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biohys. Acta* 1150: 9 (1993) These Stealth® liposomes have an increased circulation time and an improved targeting to tumors in animals. Woodle et al., *Proc. Amer. Assoc. Cancer Res.* 33: 2672 (1992). Human clinical trials are in progress, including Phase III clinical trials against Kaposi's sarcoma. Gregoriadis et al., *Drugs* 45: 15 (1993). Antisense polynucleotides and expression vectors can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, and U.S. Pat. No. 4,975,282, all of which are hereby incorporated by reference.

Liposomes can be prepared for targeting to particular cells or organs by varying phospholipid composition or by inserting receptors or ligands into the liposomes. For instance, antibodies specific to tumor associated antigens may be incorporated into liposomes, together with antisense polynucleotides or expression vectors, to target the liposome more effectively to the tumor cells. See, for example, Zelphati et al., *Antisense Research and Development* 3: 323–338 (1993), describing the use "immunoliposomes" containing antisense polynucleotides for human therapy.

In general, the dosage of administered liposome-encapsulated antisense polynucleotides and vectors will vary depending upon such factors as the patient's age, weight, height, sex, general medical condition and previous medical history. Dose ranges for particular formulations can be determined by using a suitable animal model.

The above approaches can also be used not only with antisense nucleic acid, but also with ribozymes, or triplex agents to block transcription or translation of a specific CCR2 DNA, either by masking that mRNA with an antisense nucleic acid or triplex agent, or by cleaving it with a ribozyme.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1(3):227, 1991; Helene, C., *Anticancer Drug Design,* 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260:303, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Treatment with Bone Marrow Cells or CD4+Cells from CCR-64I Donors

According to embodiments of the invention, treatment or prevention of HIV-1 infection is achieved by introduction into a patient of CD4+cells or bone marrow cells derived from donors.

Delivery of the Therapeutic Agents to a Patient

Delivery of any of the above therapeutic agents, antibodies, or antisense oligonucleotides, receptor ligands, or isolated cells, would require administration to the patient of therapeutically effective does. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patent, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are preferably administered intravenously. However, other routes of administration are within the scope of the inventor. Thus, the pharmaceutical compositions can be administered topically, intravenously, orally or parenterally or as implants, but even rectal use is possible in principle. Suitable solid or liquid pharmaceutical preparation forms are, for example, granules, powders, tablets, coated tablets, (micro) capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249: 1527–1533 (1990), which is incorporated herein by reference.

The pharmaceutical compositions according to the invention may be administered locally or systemically. By "therapeutically effective dose" is meant the quantity of a compound according to the invention necessary to prevent, to cure of at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) GOODMAN AND GILMAN'S: THE PHARMACOLOGICAL BASES OF THERAPEUTICS, 8th ed., Pergamon Press; and REMINGTON'S PHARMACEUTICAL SCIENCES, 17th ed. (1990), Mack Publishing Co., Easton, Pa., each of which is herein incorporated by reference.

Detection of the CCR2-64I Allele

Determination of the likelihood of an initial HIV infection to be sustained in a subject, to lead to AIDS, and the likely rate of the disease's development leads to more rational choices of treatment. Diagnostics are enabled by the present invention in that it is recognized that the progression is inhibited in individuals with the CCR2-64I allele. The diagnostic methods enabled by the present invention can be generally regarded as of two types. Diagnostics using nucleic acid primers for amplification of a nucleic acid or hybridization probes, and diagnostics employing antibodies directed to the CCR2 receptor or the product of the CCR2-64I gene. In addition, identification of CCR5Δ32 can also be accomplished by such methods. The amplification of a nucleic acid can be accomplished by one of a number of methods known to one skilled in the art. By way of example, amplification by PCR is described below.

PCR Based Diagnostics

The allelic profile of a patient can be determined by employment of PCR technology. The target nucleic acid to be amplified by PCR would be either the CCR2 RNA (through the production of cDNA) or, in a preferred embodiment, the CCR2 gene. Primers would be designed on sequences at position 64 of the corresponding amino acid sequence. By judiciously choosing primers and reaction conditions, one can obtain a fragment which is indicative of the presence or absence of the mutation. One skilled in the art would recognize variations on this motif. For example, the PCR reaction may contain labeled oligonucleotides to facilitate subsequent detection of the PCR product. The label can be, for example, radiolabeled nucleotides, or biotin incorporating nucleotides. According to such a diagnostic procedure employing PCR, either wt or 64I homozygote will produce a product of a discrete, expected size when appropriate primers are used. A heterozygous individual will be identified by reaction with both a set of primers directed to the wt allele and a set of primers directed to the 64I allele.

Hybridization-Probe Based Diagnostics

An oligonucleotide can be designed which under known experimental conditions can form a stable hybrid with a target nucleic acid sequence. Typically, such experimental conditions include incubation in high salt at 65° C., or incubation of 42° C. in the presence of formamide, although one skilled in the art can readily define other experimental conditions to allow stable hybrid formation. Consideration as to the optimum size of the hybridizing oligonucleotide under a set of experimental conditions are well known to one skilled in the art (see Maniatis et al., supra).

Typically, oligonucleotides would be between 12 and 25 nucleotides in length, though use of shorter and longer oligonucleotides is possible. In a typical hybridization probe based diagnostic test, the targeted nucleic acid is blotted on a membrane. Alternatively, the target nucleic acid is digested by restriction endocleases, electrophoresed on a gel, and then blotted onto a membrane. The hybridizing probe is labeled (typically by incorporating radionucleotides).

In one embodiment, the probe would be tested on a blot of restriction enzyme digested, size separated DNA. The pattern of the hybridizing bands would be informative as to the allelic status of the DNA. For example, the wt DNA contains a particular restriction enzyme cleavage site within the sequence corresponding to amino acid position 64. This particular restriction enzyme cleavage site is not contained in the CCR2-64I sequence. DNA is digested with the restriction enzyme, electrophoresed, blotted, and probed with a CCR2 probe. A different pattern will result if the tested individual contains the 64I allele versus the wild-type allele. If the individual contains both the 64I and the wild-type allele, both patterns will be evident.

Diagnostics Based on the Use of Antibodies

Antibodies and monoclonal antibodies directed to CCR2 or CCR2-64I receptors can be obtained by methods disclosed above. In a preferred embodiment, blood serum samples derived from the patient is treated by standard methods to disrupt the cells, which can then be followed by a limited purification of the sample. The product is then analyzed by ELISA. Alternatively the crude preparation is run on a polyacrylamide gel blotted onto membranes, and assayed by Western Blotting. At this point, separate use of the anti-CCR2 antibody and the anti-CCR2-64I antibody can reveal the homozygous or the heterozygous condition. Such methods of partial purification of an extract and ELISA and Western blotting are well-known to one of skill in the art (see Maniatis, supra).

It should be noted that HIV-like viruses are responsible for disease in mammals other than humans. By extrapolation from the above observations, and knowledge as to chemokine receptors in other mammals, the present invention relates to equivalent therapies and diagnostic methods in mammals, generally. In a preferred embodiment, the patient is human.

It is understood that detection of the CCR5Δ32 allele is also accomplished by the above methods and may optionally be employed for further allele profile analysis.

EXAMPLES

Example 1

A Frequent CCR2 Gene Polymorphism

To identify alternations in chemokine receptor genes that might influence HIV-1 infection and/or progression, we screened the entire CCR2 gene for variants using the single-strand conformation polymorphism (SSCP)/heteroduplex assay (HA) methods. For this method, the coding region of the CCR2 gene was amplified with primers CCR2F3 5' ATGCT GTCCA CATCT CGTTC (SEQ ID NO:3) and CCR2R3 5' CCCAA AGACC CACTC ATTTG (1-327 bp) (SEQ ID NO:5); CCR2F4 5' ATTAC TCTCC CATTG TGGGC (SEQ ID NO:5) and CCR2R4 5' GGAAA TTATT CCATC CTCGTG (277-604 bp) (SEQ 10 ID NO:6); CCR2F1 5' TTCTG TTTAT GTCTG TGGCC (SEQ ID NO:7) and CCR2R6 5' GATTG ATGCA GCAGT GAGTC (555-904 bp) (SEQ ID NO:8); CCR2F5 5' CCAAG CCACG CAGGT GACAG (SEQ ID NO:9) and CCR2R5 5' TTATA AACCA GCCGA GACTT (852-1083 bp) (SEQ ID NO:10). The products were resolved on 6% acrylamide gels (37.5:1 acrylamide:bis-acrylamide) containing 10% glycerol at room temperature. A G-A nucleotide substitution was detected at position 190 (counting from the ATG start codon) that substitutes the CCR2-+ amino acid residue 64-valine to 64-isoleucine, a conservative change located within the first transmembrane domain of the CCR2 receptor (see FIG. 1 where 1/1, 1/2, and 2/2 is CCR2-+/+, +/64I and 64I/64I respectively). Using both SSCP and a converted PCR-RFLP assay (an introduced BsaBI restriction site which includes the variant nucleotide) the allele and genotype frequency of 3041 individuals included in five prospective AIDS cohorts was determined (Table 1). Genotypes were determined by single-strand conformation polymorphism (SSCP) and with a PCR-RFLP assay using a BsaBI site introduced into the PCR primer next to the C-T transition which encodes the CCR2-64I polymorphism. Amplification with the primers CKR12_1A: 5'TTGTGGGCAACATGATGG (SEQ ID NO:11), which has a cytosine substituted with an adenine (in lower case), and CKR2_1Z: 5'GAGCCCACAATGG-GAGAGTA (SEQ ID NO:12) generated a 128 bp product. Digestion with BsaBl yields a 100 and 18 bp fragments when an isoleucine was present instead of valine at position 64 in CCR2. These products were genotyped on 4% AMRESCO 3:1 biotechnology grade agarose TBE gels. The alternation CCR2-64I was found to be common in all ethnic groups with allele frequencies from 10–29%.

Figures 1, 3A:
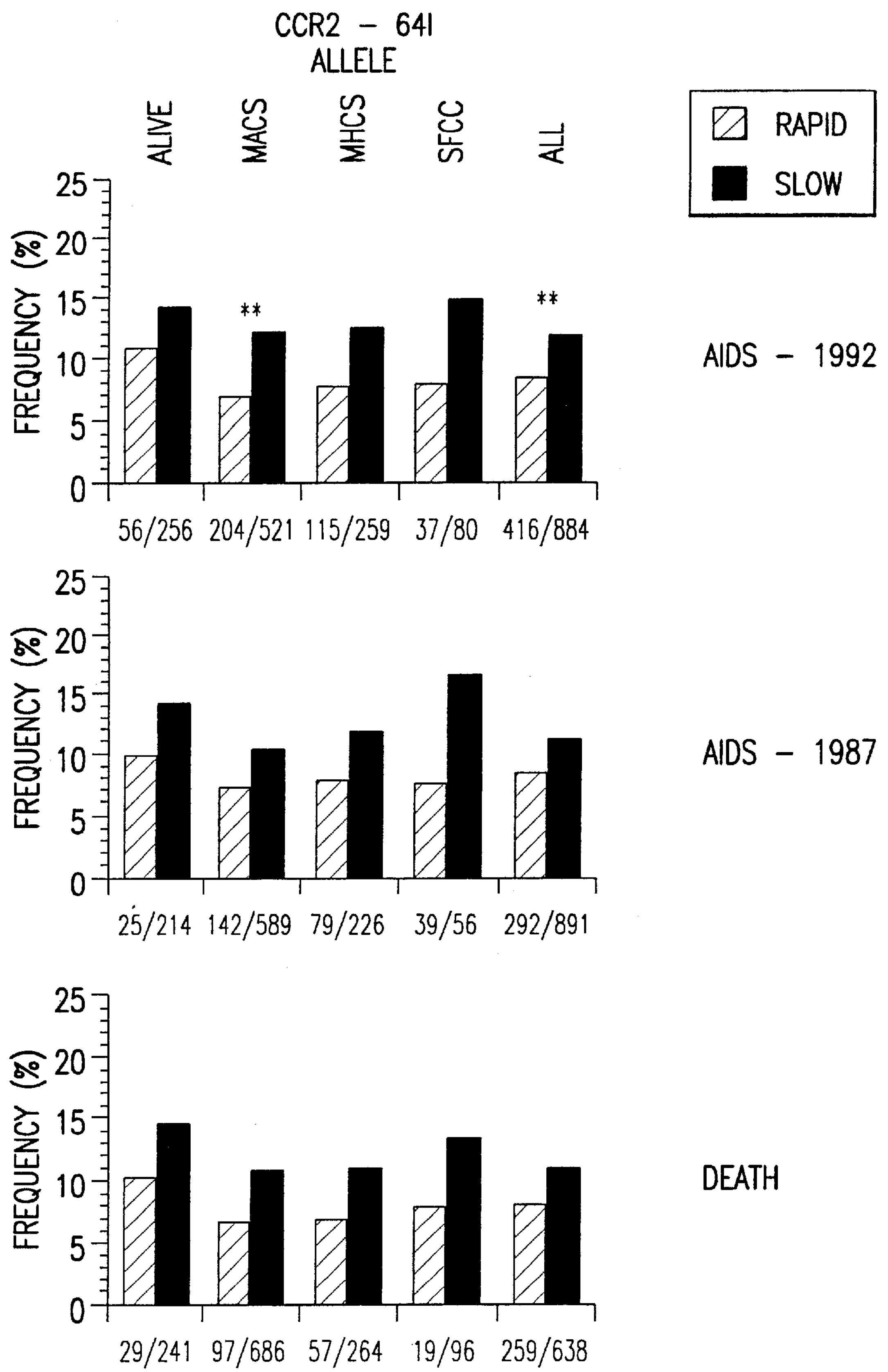
FIGS. 3A and 3B show an analysis of allele CCR2-64I and genotype frequencies with reference to progression to AIDS in study cohorts.

The amino acid sequence of normal CCR2 and related human chemokine receptors, encoded by a gene cluster on chromosome 3 (M. Samson, et al., supra) were aligned. It was found that CCR2-64I causes a substitution of valine with isoleucine at position 64. In FIG. 1, the box represents transmembrane domain 1 (TM 1), and amino acid position 64 of CCR2 is designated by an arrow below the alignment. In this figure, periods represent residues that are identical to CCR2 and dashes represent gaps placed in the alignment.

Example 2

CCR2-64I Does Not Influence HIV-1 Infection

The allele frequency of CC2-64I and the CCR2 genotype frequency was examined in five clinically defined cohorts of HIV-1-exposed patients. These include two homosexual cohorts, two hemophiliac cohorts, and one I.V. drug user cohort (Table 1). There were no significant differences in CCR2 allele or genotype frequencies in comparisons of exposed uninfected (HIV−) vs. infected (HIV+) patients in any of the cohorts. A collection of 58 "extremely" high risk, exposed-uninfected individuals (those with documented receipt of HIV-1 contaminated clotting factor, or over 100 unprotected sexual encounters with infected partners) (Huang et al., (1996), *Nature Med.* 2: 1240; Detels etal, (1996), *AIDS* 10: 102; J. Goedert et al., (1996) *Am. J. Epidem.* 121: 629) also showed CCR2 allele/genotype frequencies not significantly different from HIV-1-infected individuals. The CCR2 genotype frequencies in each cohort conformed to expectations of Hardy-Wienberg equilibrium, further excluding any significant effect of CCR2-64I on HIV infection.

Example 3

CCR2 Genotype Influences AIDS Progression

A subgroup of 801 seroconverter patients (those whose date of HIV-1 infection can be estimated precisely since they enrolled in the cohort before converting from HIV-antibody negative to HIV-1-antibody positive) from four cohorts were analyzed by comparing the rate of progression to AIDS among different CCR2 genotypes using a Cox proportional hazard model (PHREG, SAS Release 6.09, SAS Institute Inc., Cary, N.C.).

Three AIDS definitions as stipulated by CDC (Center for Disease Control Morb. Mort. Wkly. Rep. 36: (suppl. 1) (Aug. 14, 1987); Center for Disease Control *Morb. Mort. Wkly. Rep.* 41 (18 December 1992) This publication contains a revised classification system for HIV infection and expanded surveillance case definition for AIDS among adolescents and adults.) (reflecting increasing morbidity) were considered as endpoints: 1) AIDS-1992 includes HIV-1 infection plus either AIDS-defining illness or decline of CD4-T-lymphocytes to $\leqq 200$ cells/$mm^3$; 2) the more stringent AIDS-1987 includes HIV-1 infection plus development of AIDS pathology; and 3) death during follow up for an HIV-1 infected patient (97% of these had AIDS-1992). The results of these analyses are illustrated in FIG. 2 and tabulated in Table 3.

Figures 2, 3A:
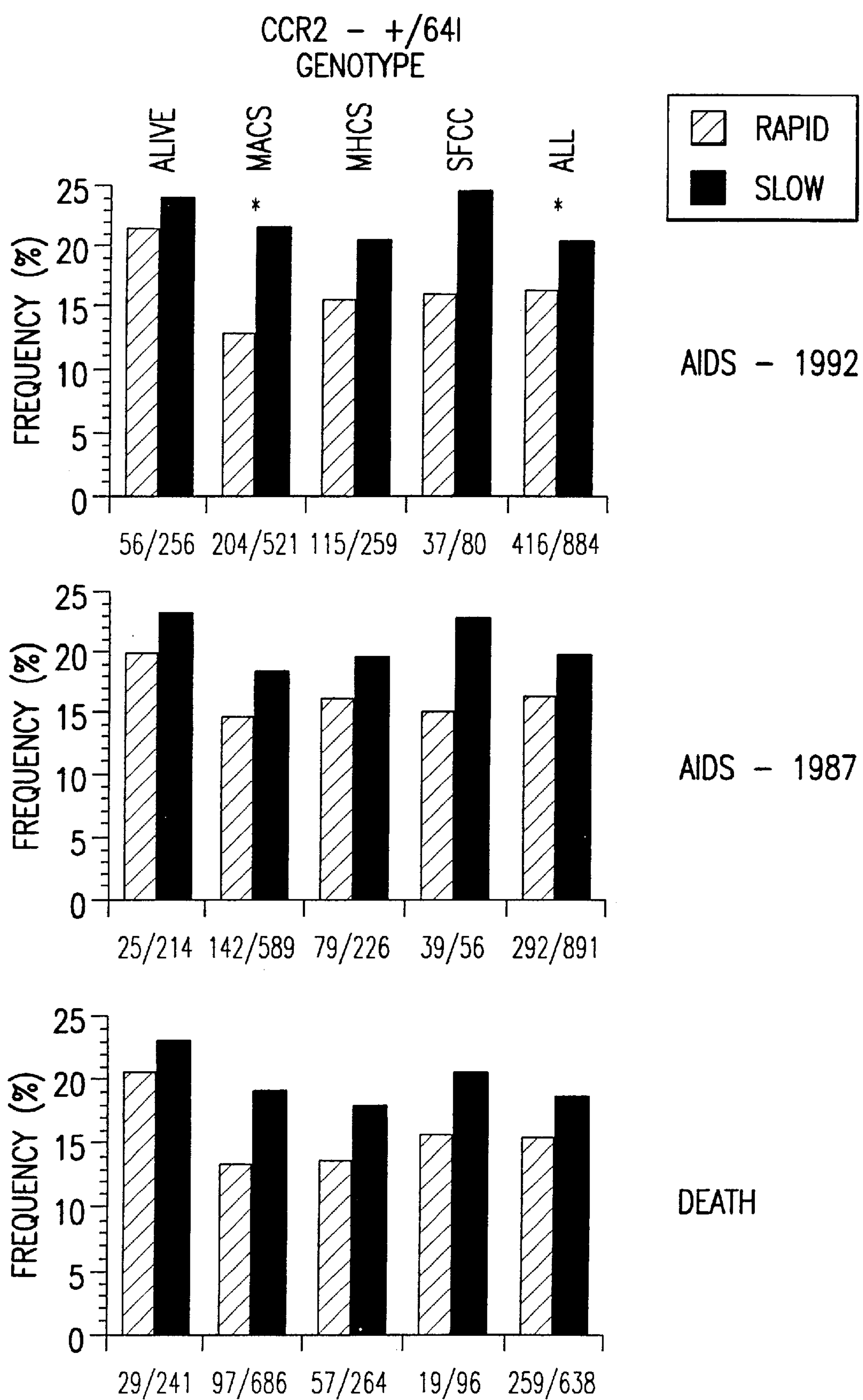

FIG. 2 shows Kaplan Meier survival curves demonstrating the dependence of progression to AIDS-1992 on CCR2 genotype in MACS, HHCS and combined "All" cohort analyses. In the studies, all patients were seroconverters with a maximum 3-year interval between an HIV-antibody negative visit and a first HIV-1 antibody positive test note: n=number of patients; p=statistical p-value; and RH=relative hazard based on the Cox proportional hazard models).

For three cohorts (MACS, MHCS, and SFCC) plus the combined cohort analysis, a consistent 2–3 year postponement of AIDS outcomes (by each definition) was observed for CCR2-+/64I plus CCR2-64I/64I genotypes compared to patients homozygous for the normal CCR2-+/+ allele. The CCR2 genotypic protection was statistically significant for combined analysis with AIDS-1987 and AIDS-1992 endpoints as well as for AIDS-1992 for the SFCC homosexual cohorts. The ALIVE cohort, which is composed of 94% African Americans, did not show a CCR2 genotype association in the survival analysis (but see category analysis below). When Caucasian participants alone were examined, the combined analysis showed significant (or highly significant) CCR2 postponement of AIDS for each clinical AIDS definition. The relative hazard for significant Caucasian seroconverters ranged from 0.64–0.67, indicating that individuals with a CCR2-+/+ genotype progress to AIDS 50% more rapidly than patients carrying the CCR2-64I allele.

A dramatic demonstration of the protective effect exerted by the CCR2-64I allele and included genotypes is presented by a defined disease category analysis (FIG. 3*a*). Because the four cohorts had no significant difference in either CCR2 allele or genotype frequency, they were pooled to test for significant difference between rapid and slow/non-progressors. In addition, CCR2-64I containing genotypes were higher in all cohorts for all outcomes for 24 comparisons (2 genotypes, 4 cohorts, 3 outcomes). Since these outcomes are interdependent, we applied a sign test to 8 comparisons (4 cohorts, 2 genotypes) to detect $p \leqq 0.004$.

Figures 1, 3B:
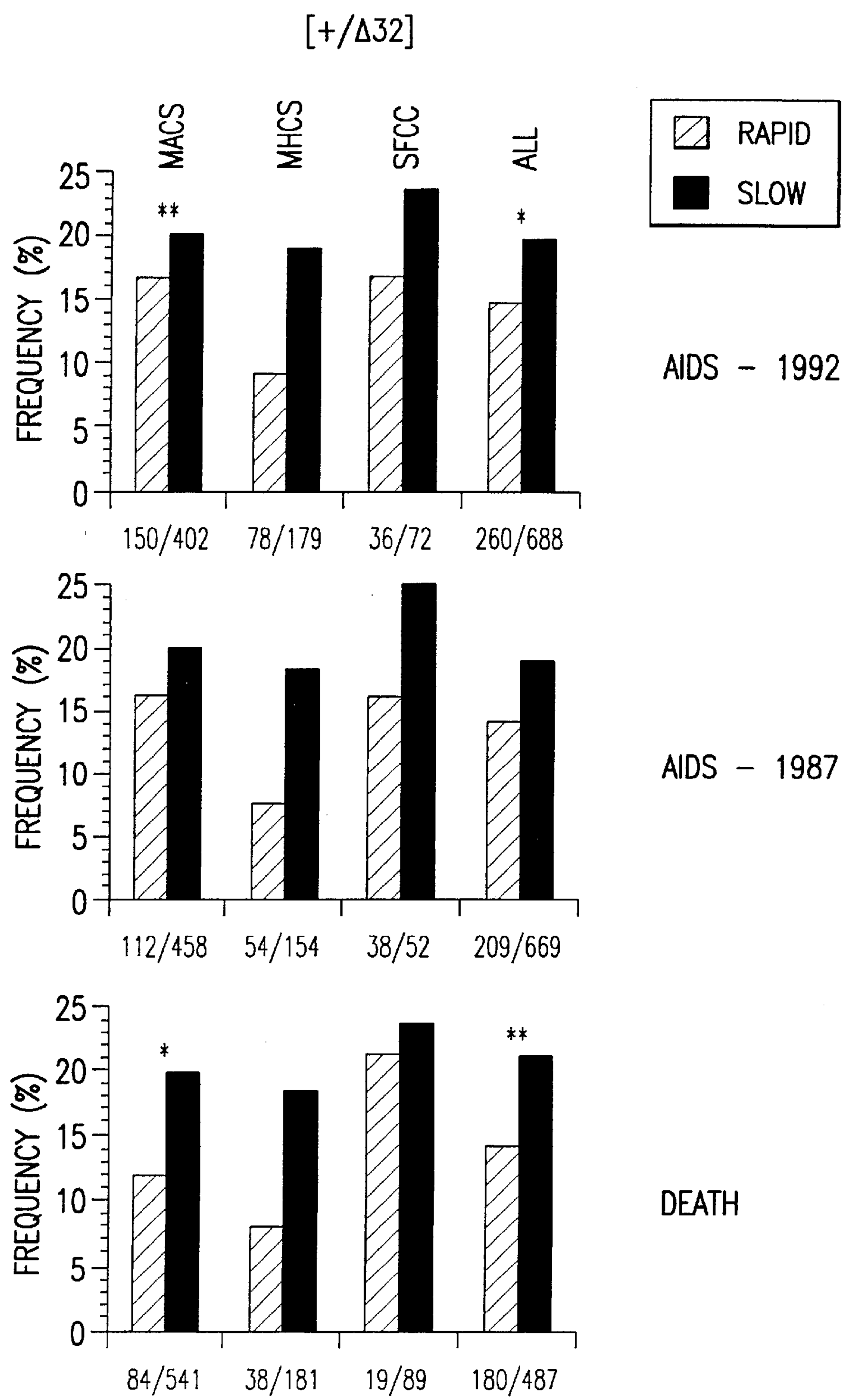
Figures 2, 3B:
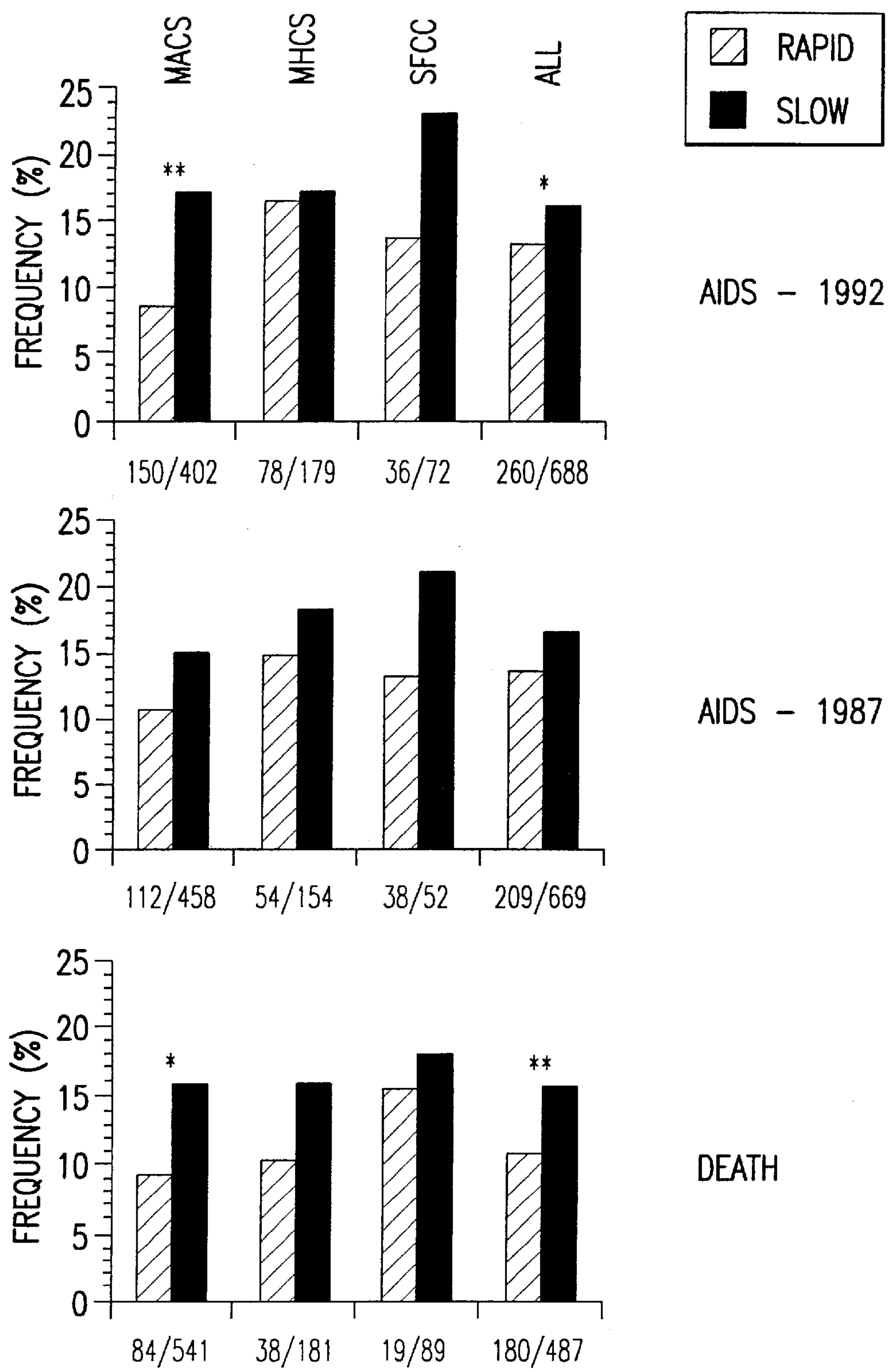

FIG. 3A shows this analysis of allele CCR2-64I and genotype frequencies with reference to progression to AIDS in each cohort and in all patients based on three AIDS endpoints (see text). Seroconverters who progressed to designated outcomes before the cutoff time were compared to seroconverters plus seroprevalents who survived outcome-free for at least that long. Cutoffs, in years, were chosen as the time where approximately half the seroconverters had progressed to the outcome, such that ALIVE and MACS-6 years; MHCS-9 years; SFCC-12.5 years; All cohorts-8 years (Goeder, 1989, N. Engl. J. Med. 321:1141; Valhov, D., et al., 1991, NIDA Research Monograph Series 103(Public Health Service, alcohol and Drug Abuse Administration, Washington, D.C.; Kaslow, R., et al, 1987, Am. J. Epidem. 126: 310; Phair, J., et al, 1992, J. AIDS 5:490). Note that in the figure the number of patients in each disease category is listed below the bar graph. The $X^2$ analyes of alleles and genotypes had one and two degrees of freedom, respectively. In this figure, p-values of less than 0.05 are marked with *, and those below 0.01 with II. FIG. 3*a* shows CCR2 allele and genotype frequencies in cohorts for different AIDS endpoints. In all four cohorts for all three outcomes longer term survivors had higher CCR2-64I allele frequencies than more rapid progressors. Similarly in all comparisons, the CCR2+/64I and 64I/64I genotypes are more frequent in the longer term survivors which has a binomial sign test $p=6\times10^{-8}$. FIG. 3*b* CCR2-+/+; CCR5+/Δ32 genotype incidence is defined disease categories (left) and CCR2-+/64I; CCR5-+/+ genotype incidence in defined disease categories (right).

Figures 1, 4A:
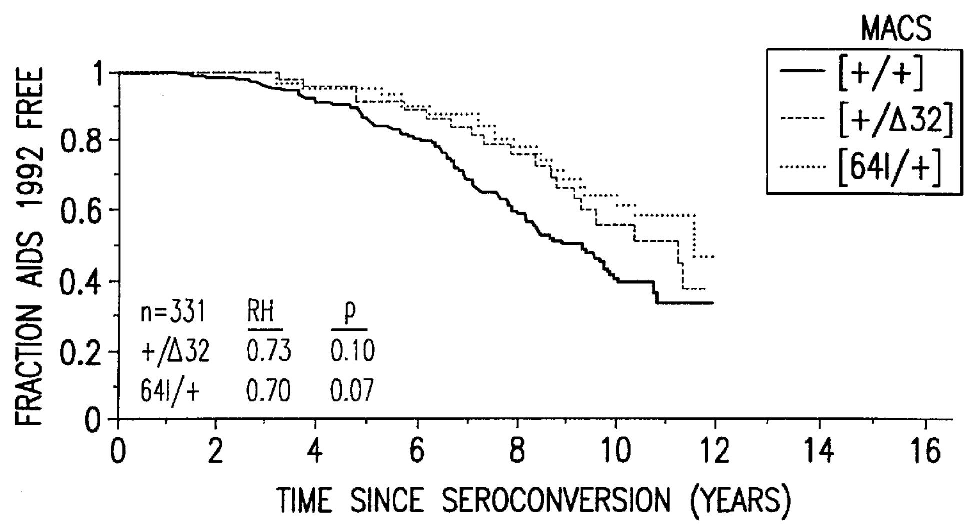
FIGS. 4*a*(1–3) are Kaplan-Meier survival plots of time to AIDS.
Figures 2, 4A:
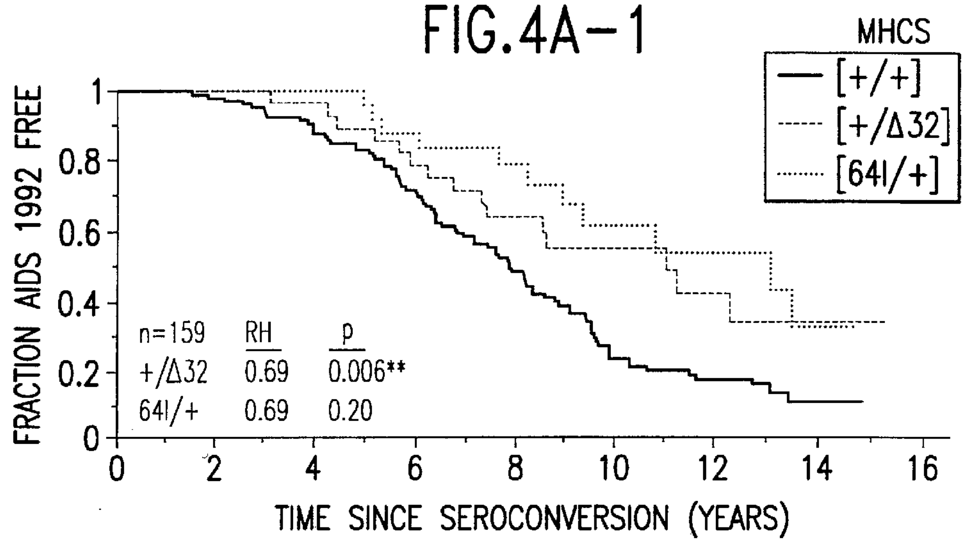
Figures 3, 4A:
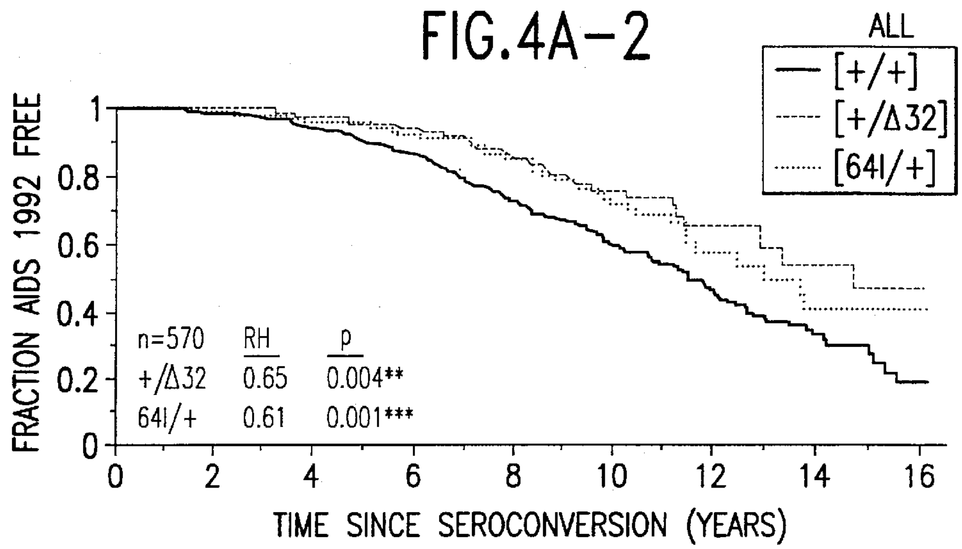

Each individual cohort plus combined cohorts were divided into relatively rapid progressors vs. slow progressors based upon the mid-point of their survival distribution. The CCR2-64I allele frequency was invariably lower among rapid progressors to AIDS than in the slow or non-progressor group who avoid AIDS (by each clinical definition) for greater than 6–12.5 years after infection. This analysis included some 1300 patients, and the cohorts show a 40–120% increase in CCR2-64I allele frequency in the slow/non-progressor category (FIG. 4*a*). Similarly, when the frequency of CCR2-+/64 genotypes is compared among disease categories, the heterozygote genotype frequency is greater in the slow/non-progressor categories for 12 of 12 comparisons (4 cohorts, 3 AIDS outcomes).

Example 4

CCR2 and CCR5 Interaction

CCR5-Δ32/+ heterozygotes also demonstrate a slower progression to AIDS based on studies of these same cohorts (M. Dean et al., (1996) *Science* 273, 1856) plus two other confirmatory studies (Huang et al., (1996) *Nature Med* 2: 1240; N. L. Michael et al., (1997) *Nature Med.* 3: 38; Biti et al., (1997) *Nature Med.* 3:253). Since the CCR2 and CCR5 loci are very tightly linked (approximately 18 kb apart) on chromosome 3 (M. Dean et al., (1996) *Science* 273, 1856; M. Samson et al., (1996) *Biochemistry* 35: 3362; J. Goedert et al., (1996) *Am. J Epidem.* 121: 629), we examined the co-occurrence and genotypic independence of CCR5 and CCR2 alleles among patients from the same cohorts (Table 4). Analysis of the two locus genotypes for 2904 patients showed that three genotypes (CCR2-64I/64I, CCR5-+/Δ32; CCR2-+/64I, CCR5-Δ32/Δ32; and CCR264I/64I; CCR5-Δ32/Δ32) were absent, indicating that the mutant alleles occur on different chromosomal haplotypes that are in strong (perhaps complete) linkage disequilibrium with each other. As a consequence of the tight chromosomal linkage plus alternative haplotypes carrying each mutant allele, the two mutant haplotypes (CCR2-+)-(CCR5-Δ32) and CCR2-64I)-(CCR5+) plus the two-locus normal haplotype (CCR2-+)-(CCR5-+) can be considered as 3 alleles of a combined CCR2/CCR5 compound locus. Three tractable genotypes of the compound locus are designated as [+/+]; [+/Δ32]; and [64I/+] representing (CCR2-+/+; CCR5-+/+); (CCR2-+/+; CCR5-+/Δ32); and (CCR2-+/64I; CCR5+/+) genotype, respectively.

In FIG. 4*a* a survival analysis of the effect of both CCR2 and CCR5 genotype on progression to AIDS-1992 and on progression to death for two cohorts (MACS and MHCS) plus a combined analysis of all seroconvertors is presented. The Cox proportional hazard model revealed significant postponement of AIDS onset for CCR23-64I containing genotypes and also for CCR5-Δ32 containing genotypes compared to the [+/+] individuals, homozygous for normal alleles at each locus. FIG. 4*a* illustrates the extent of protection afforded by CCR5-Δ32 heterozygosity and CCR2-64I heterozygosity of homozygosity, with the effect of mutant alleles at the other locus subtracted. Both CCR5-Δ32 and the CCR2-64I allele-containing genotypes were significantly associated with delayed onset of AIDS-1992 or death.

Figures 1, 4B:
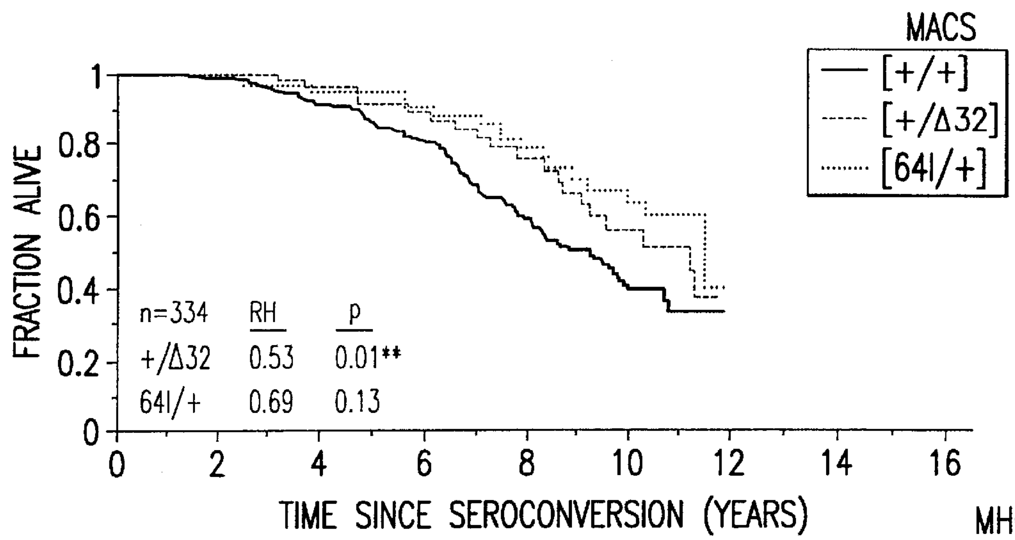
FIGS. 4*b*(1–3) are Kaplan-Meier survival plots for death as an endpoint.
Figures 2, 4B:
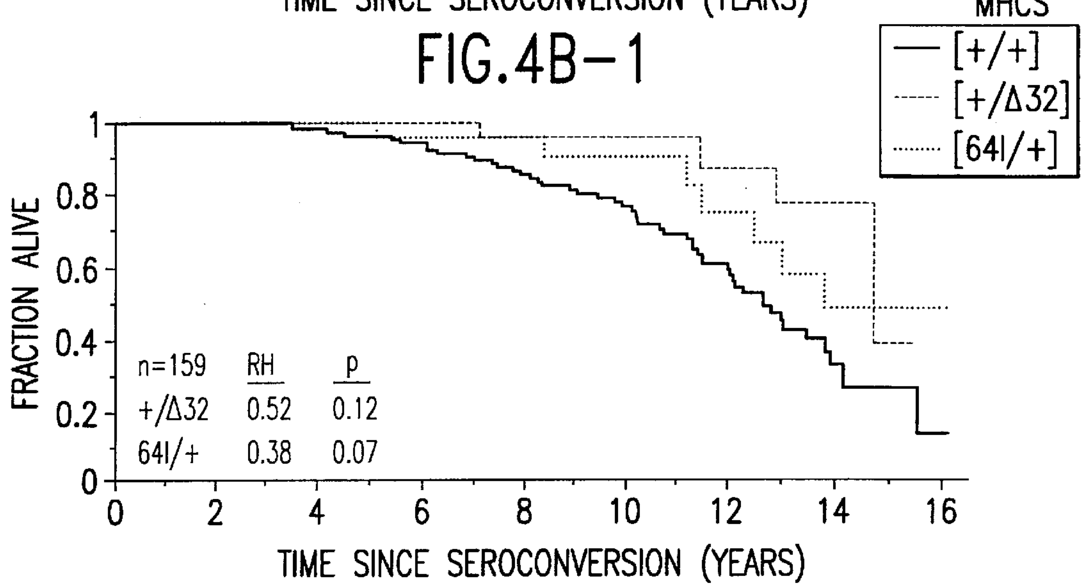
Figures 3, 4B:
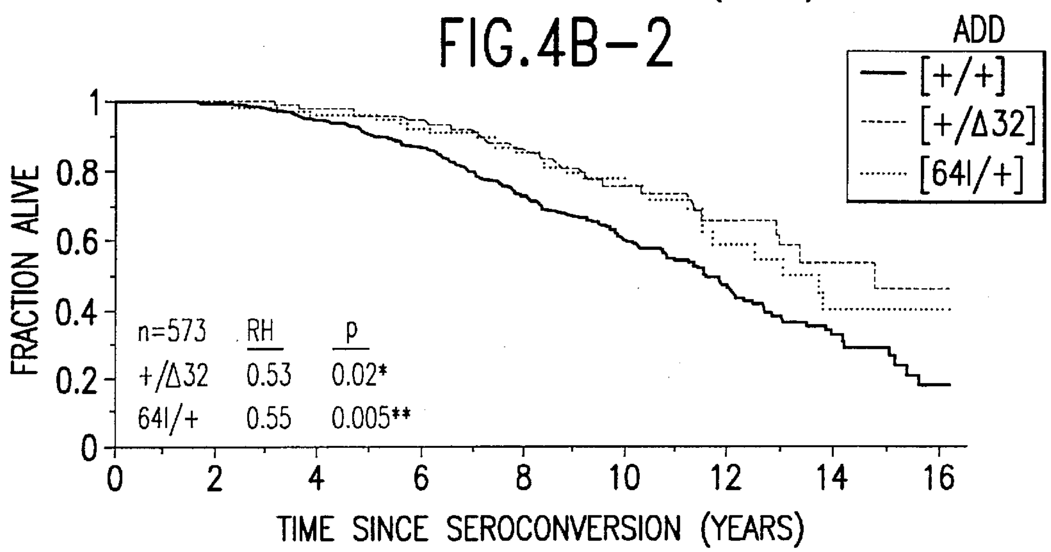

A statistical analysis of each cohorts's survival curves are presented in Table 5 as three parts: I) CCR5-+/Δ32 vs. CCR5-+/+ for all seroconvertors; II) compound CCR2-CCR5 locus genotype classes, [+/+], [+/Δ32] and [64I/+], as illustrated in FIGS. 4*a* and 4*b*; and III) combined analysis of CCR2+/+; CCR5+/+ vs. all mutant genotypes at either locus. These data affirm the protective effects of CCR5 previously reported (M. Dean et al., (1996) *Science* 273, 1856); Huang et al., (1996) *Nature Med.* 2:1240; N. L. Michael et al., (1997) *Nature Med.* 3: 338; Biti et al., (1997) *Nature Med.* 3: 253) plus show that the CCR2-64I protection is equally as strong and independent of the CCR5-+/Δ32 influence. The CCR2 effect becomes even greater when the CCR5-+/Δ32 subjects are removed (Part II in Table 5 compare to Table 3) since the distortion becomes highly significant for combined cohort analyses for each AIDS endpoint (RH=0.55–0.62). The CCR5-Δ32 effect is also retained when CCR2-64I containing genotypes are subtracted (RH-0.61–0.79 for all cohorts). When mutant genotypes for CCR2 and CCR5 are consistent together, the result is additive producing statistical significant for genetic influence as high as $8.0\times10^{6}$ for combined cohort progression to AIDS-1992 (Part III in Table 5). Individuals with mutant genotype at either CCR2 or CCR5 show hazards relative to normal of 0.48–0.72 in statistically significant analyses.

A defined disease category analysis using compound two locus genotypes (FIG. 3*b*) show that the heterozygote frequencies for both CCR2 and CCR5 mutant haplotypes are elevated in long term survivors relative to the rapid progressors. As for the analysis for CCR2 separately (FIG. 3*a*), the protective effects of CCR2 and CCR5 mutant alleles are significantly greater among patients for both AIDS-1992 and death with combined cohort analyses plus the MACS cohort alone (FIG. 4*b*). The mutant alleles, CCR2-64I and CCR5-Δ32 and genotypes containing them are less frequent in more rapid progressors in all three cohorts and considering all three AIDS outcomes (a total of eighteen comparisons). A conservative sign test was applied to three genotypes and three cohorts. For only one outcome there was a significant excess of [+/Δ32], [64I/+] and [64I/64I] (FIG. 3*b*; p=0.002). The overall trend for alleles and genotypes at both CCR5 and CCR2 are consistent with the protective effects seen for these alleles in the survival and defined disease category analyses.

Figure 5A:
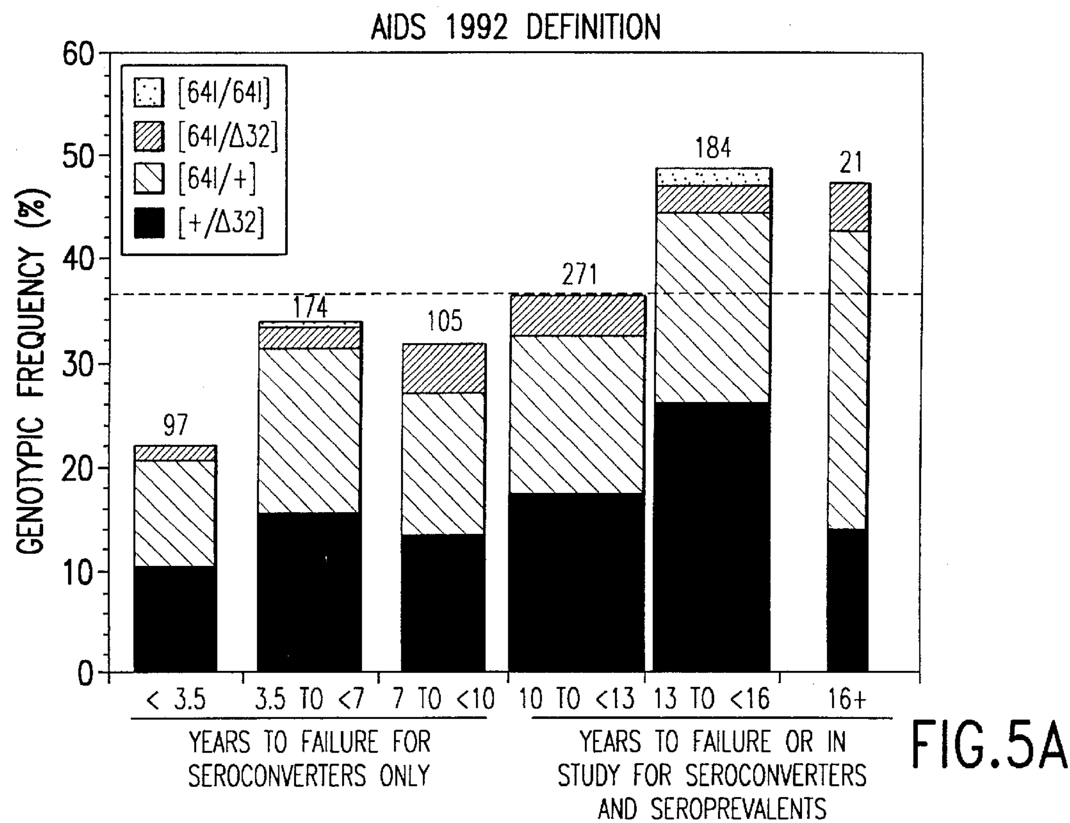
FIGS. 5A–5C demonstrate the frequencies of the protective genotypes ([+Δ32], [+/64I],[64I/Δ32], [64I/64I]) in six categories of increasing survivorship during HIV-1 infection.
Figure 5B:
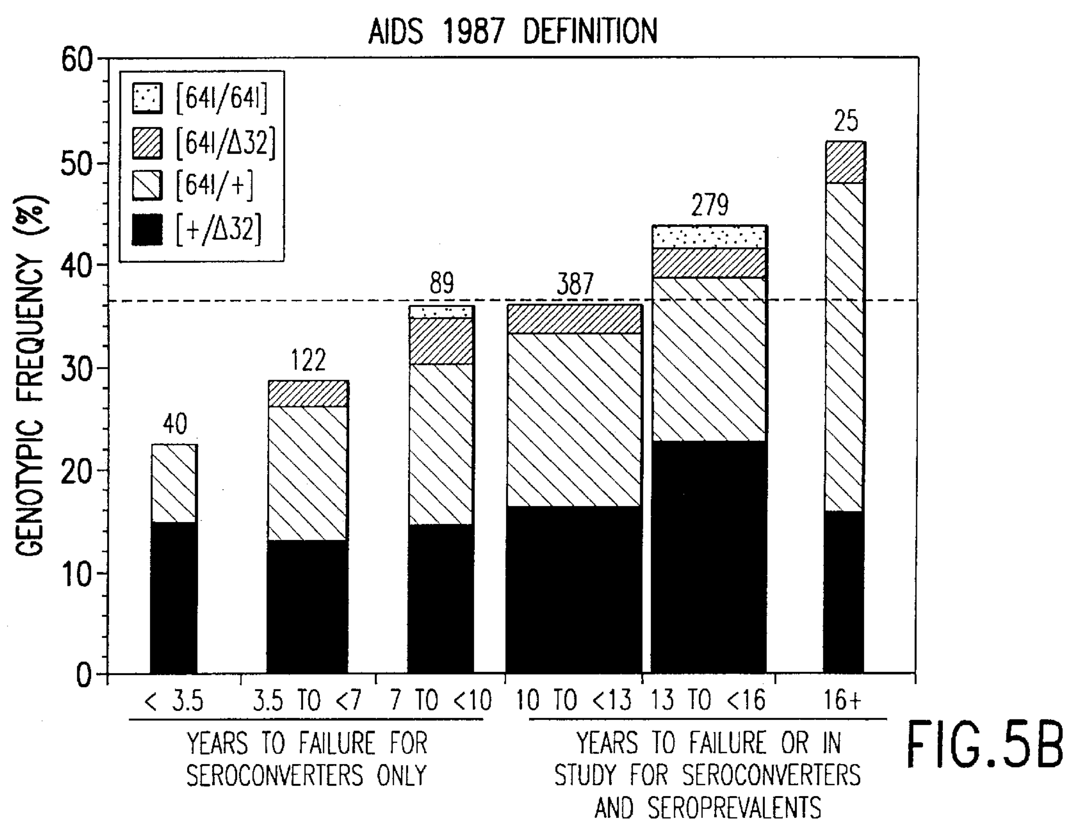
Figure 5C:
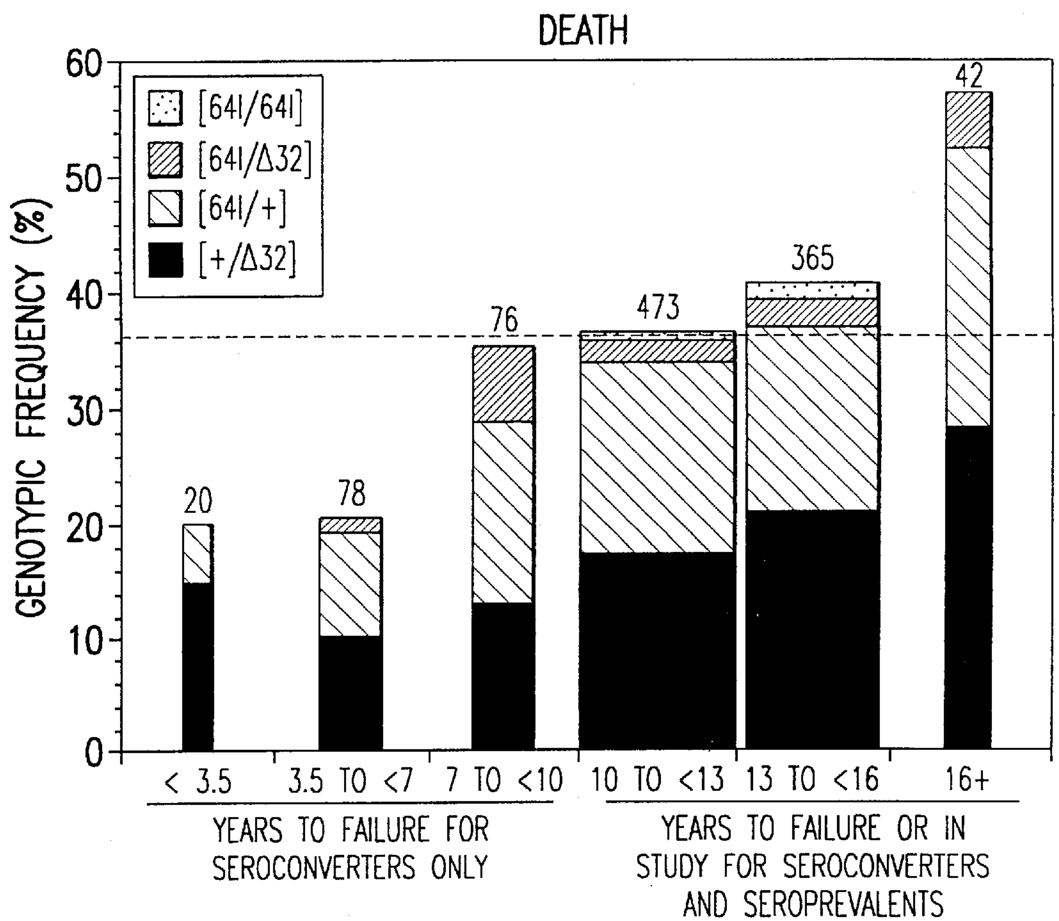

The additive effects of CCR2 and CCR5 mutant alleles is illustrated in FIG. 5 where the incidence of composite mutant genotypes in six intervals after HIV-1 infection are considered. FIG. 5 shows the frequencies of the protective genotypes ([+/Δ32], [+/64I], [64I/Δ32], [64I/64I]) in six categories of increasing survivorship during HIV-1 infection. Genotypic frequencies were calculated separately for time to (A) AIDS-1992 200, (B) AIDS 1987 and (C) death, from seroconverters which was less than 3.5, 3.5 to less than 7 and 7 to less than 10 years. In addition, genotypic frequencies were calculated for seroconverters and seroprevalents whose time to the outcome was 10 to less than 13, 13 to less than 16 and 16 years or greater. The number of people (n) observed in each category is shown above each column and its width is proportional to the square root of n. The average frequency of these variants in Caucasians is shown as a dotted line for comparison of progression categories. Contingency tests of the three common genotypes ([+/+], [+/Δ32], and [+64I]) were performed for time to AIDS 1992 ($X^2$=26.43, 10 d.f., p=0.003), AIDS 1987 definition ($\chi^2$=18.60, 10 d.f., p=0.05) and death($X^2$=21.65, 10 d.f., p=0.017). Contingency tests of +/+ versus all others for time to AIDS 1992 ($X^2$=24.50, 5 d.f. p=0.002), AIDS 1987 definition ($X^2$=14.61, 5 d.f., p=0.01), and death ($X^2$=21.17, 5 d.f., p=0.0008) were also performed.

The results show a marked increase of mutant genotypes for both CCR2 and CCR5 among patients that survive without progressing to AIDS over longer periods. The elevated heterozygote frequency for the two loci in long term survivors emphasize the additive protective effect of both loci. The increase in observed mutant genotype (either CCR2 or CCR5) frequency over the observed mutant frequency in all patients (36% dotted line in FIG. 5) allows an estimate of the fraction of long-term survivors (≧16 years without progressing to AIDS) that can be attributed to CCR2/CCR5 genetic factors. For the three AIDS endpoints that value is: 32% for AIDS-1992; 43% for AIDS-1987 and 57% for death.

TABLE 1

CCR2-641 allele frequencies among five AIDS cohorts and in ethnic groups*

| | Risk group (reference) | No. Patients Genotyped | CCR2-641 Allele Frequency |
|---|---|---|---|
| AIDS Cohorts | | | |
| ALIVE | Intravenous drug user (37) | 755 | 0.147 |
| HGDS | Hemophiliac (41) | 265 | 0.151 |
| MHCS | Hemophiliac (36) | 700 | 0.109 |
| MACS | Homosexual men (38,39) | 1098 | 0.101 |
| SFCC | Homosexual men (40) | 223 | 0.130 |
| Ethnic | Caucasians | 1862 | 0.099 |
| Groups | African Americans | 905 | 0.150 |
| | Hispanics | 204 | 0.172 |
| | Asian | 14 | 0.286 |

*Patient race was determined from the clinical records of the cohorts examined with those noted as other excluded from the racial frequency calculations. The cohorts that were examined were: the AIDS Link to the Intravenous Experience (ALIVE), Human Growth and Development Study (HGDS), Multicenter AIDS Cohort Study (MACS), Multicenter Hemophiliac Cohort Study (MHCS) and San Francisco City Clinic Study (SFCC). Patient genotypes were determined from DNA extracted from immortal lymphoblastoid B-cell line established for each patient (16).

TABLE 2

Lack of protection from HIV-1 infection by the CCR2-64I polymorphism. Each of five cohorts is shown separately along with an analysis of all patients combined. Total number (N) of patients, and percentages of alleles and genotypes are shown along with a $X^2$ analysis of infected (HIV+) and uninfected (HIV−) individuals. Caucasians who were highly exposed in the MACS, MHCS, and SFCC cohorts were compared with the HIV-1 infected Caucasians from the same cohorts, excluding CCR5-Δ32/Δ32 homozygotes.

| | | CCR2 Alleles | | | | | Genotypes | | | | |
|---|---|---|---|---|---|---|---|---|---|---|---|
| Cohort | status | N | + | 64I | $X^2$ | (P) | +/+ | +/64I | 64I/64I | $X^2$ | (P) |
| ALIVE | HIV− | 128 | 85.5 | 14.5 | 0.00 | (0.96) | 72.7 | 25.8 | 1.6 | 0.05 | (0.98) |
| | HIV+ | 625 | 85.2 | 14.8 | | | 72.5 | 25.4 | 2.1 | | |
| HGDS | HIV− | 83 | 84.9 | 15.1 | 0.08 | (0.77) | 74.7 | 20.5 | 4.8 | 2.67 | (0.26) |
| | HIV+ | 172 | 86.3 | 13.7 | | | 73.8 | 25.0 | 1.2 | | |
| MACS | HIV− | 20 | 95.0 | 5.0 | 0.63 | (0.43) | 95.0 | 0.0 | 5.0 | 3.44 | (0.18) |
| | HIV+ | 1068 | 89.9 | 10.1 | | | 80.9 | 18.1 | 1.0 | | |
| MHCS | HIV− | 169 | 90.5 | 9.5 | 0.70 | (0.40) | 81.1 | 18.9 | 0.0 | 1.27 | (0.53) |
| | HIV+ | 500 | 88.7 | 11.3 | | | 78.8 | 19.8 | 1.4 | | |
| SFCC | HIV− | 41 | 84.1 | 15.9 | 0.58 | (0.45) | 70.7 | 26.8 | 2.4 | 0.53 | (0.77) |
| | HIV+ | 167 | 88.0 | 12.0 | | | 77.8 | 20.4 | 1.8 | | |
| All | HIV− | 441 | 87.6 | 12.4 | 0.14 | (0.71) | 77.1 | 21.1 | 1.8 | 0.05 | (0.82) |
| | HIV+ | 2532 | 88.2 | 11.8 | | | 77.6 | 20.9 | 1.5 | | |
| Highest | HIV− | 58 | 87.1 | 12.9 | 2.60** | (0.12) | 77.6 | 19.0 | 3.4 | 0.23 | (0.63) |
| Risk* | HIV+ | 1600 | 90.1 | 9.9 | | | 81.0 | 18.1 | 0.8 | | |

High risk HIV− are uninfected patients from MHCS, SFCC, and MACS with documented very high exposure of clotting factor IX or over 100 unprotected sex episodes with HIV-1 infected partners (18, 36,40).

*Results of G test

TABLE 3

Survival analysis for progression to AIDS among HIV-1 infected individuals as a function of CCR2 genotype. Seroconverters of all racial groups were analyzed for the ALIVE, DCG, MACS, MHCS and SFCC cohorts, and the combination of all the cohorts. HGDS was excluded since this cohort only has seroprevalent individuals. CCR2-64I/+ heterozygotes are grouped with the homozygote CCR2-64I/64I, which was infrequent. A $X^2$ (1 d.f.), p, and relative hazard (RH) were calculated for each variable in the analysis of AIDS outcomes. Time to AIDS-1992, AIDS-1987, and death were calculated from their last negative HIV-1 antibody test. Individuals whose time between their last negative and first positive HIV-1 antibody tests was less than or equal to three years were analyzed in a Cox proportional hazard analysis where first positive was used as the truncation time (42). Analyses were age adjusted for those individuals less than thirty, thirty to forty, or more than forty years old. P values of less than 0.05 are marked with an * and those below 0.01 with **.

| | CCR2-+/+ vs. CCR2-+/64I or CCR2 64I/64I | | | | |
|---|---|---|---|---|---|
| Cohort | n | events | $X^2$ | p | RH |
| AIDS 1992 | | | | | |
| ALIVE | 126 | 57 | 0.01 | 0.93 | 1.03 |
| MACS | 402 | 293 | 1.92 | 0.17 | 0.80 |
| MHCS | 189 | 128 | 0.74 | 0.38 | 0.80 |
| SFCC | 81 | 49 | 4.21 | 0.04* | 0.44 |
| All | 798 | 487 | 5.38 | 0.02* | 0.76 |
| Caucasian | 594 | 88 | 6.95 | 0.008** | 0.70 |
| Afr. Amer. | 152 | 78 | 0.19 | 0.65 | 1.13 |
| AIDS 1987 | | | | | |
| ALIVE | 126 | 37 | 0.00 | 0.97 | 0.99 |
| MACS | 405 | 202 | 1.95 | 0.16 | 0.77 |
| MHCS | 189 | 93 | 0.02 | 0.87 | 0.95 |
| SFCC | 81 | 41 | 2.96 | 0.09 | 0.45 |
| All | 801 | 373 | 4.24 | 0.04* | 0.75 |
| Caucasian | 597 | 304 | 5.60 | 0.02* | 0.68 |
| Afr. Amer. | 152 | 53 | 0.04 | 0.85 | 1.07 |
| Death | | | | | |
| ALIVE | 126 | 28 | 0.01 | 0.93 | 0.96 |
| MACS | 405 | 153 | 0.84 | 0.36 | 0.82 |
| MHCS | 189 | 71 | 0.33 | 0.57 | 0.80 |
| SFCC | 81 | 23 | 1.57 | 0.21 | 0.44 |
| All | 801 | 275 | 2.82 | 0.09 | 0.76 |
| Caucasian | 597 | 230 | 4.89 | 0.03* | 0.67 |
| Afr. Amer. | 152 | 36 | 0.00 | 0.98 | 1.01 |

TABLE 4

Number of patients with individual composite CCR2;CCR5 genotype.*

| | | CCR2 genotype | | |
|---|---|---|---|---|
| | | +/+ | +64I | 64I/64I |
| CCR5 Genotype | +/+ | 1930/1168 | 573/289 | 50/19 |
| | +/Δ32 | 346/307 | 41/37 | 0 |
| | Δ32/Δ32 | 14/13 | 0 | 0 |

* Before slash is all patients; after slash is Caucasians only. The absence of the three genotype combinations and the frequency of double heterozygotes is consistent with the occurrence of only three CCR5:CCR2 hapolytpes: (CCR2-+)-(CCR5-+); (CCR2-+)-(CCR5-Δ32); and (CCR2-64I)-(CCR5-+). The haplotype (CCR5-64I)-(CCR5-Δ32) was never observed). The test for independence of genotypic combinations was highly significant (g = 23.22, 4 d.f., and p ≦ 0.0001).

TABLE 5

Effects of CCR2 and CCR5 genotypes on progression to AIDS outcomes in Caucasian seroconverters. Left truncated Cox proportional hazard analyses were performed in the same manner that is described in the Table 3 legend (42). CCR5; CCR2 genotypes were analyzed in three ways. (I) +/Δ32 versus +/+ for CCR5 alone. (II) CCR5 and CCR2 separated into the compound genotypes [64I/+] or [64I/64I], and [+/Δ32] versus [+/+] normal at both loci, illustrated in FIG. 4. (III) CCR5 and CCR2 grouped together such that this is an analysis [+/+] versus [+/64I], [64I/64I], [+/Δ32] or [64I/Δ32]. Caucasians from the ALIVE cohort are included in the analyses of all cohorts. P values are marked as follows: *≦0.05, ≦0.01, *≦0.001, and ****≦0.0001.

| | I. CCR5 Only | | | | | II. CCR2 and CCR5 Genotypes Separated | | | | | | | | III. CCR2 and CCR5 Grouped | | | | |
|---|---|---|---|---|---|---|---|---|---|---|---|---|---|---|---|---|---|---|
| | CCR5 - +/+ vs +/Δ32 | | | | | CCR2: [+/+] vs [64I/+] or [64I/64I] | | | | | CCR5: [+/+] vs [+/Δ32] | | | +/+] vs [+/Δ32] [64I/+], [64I/Δ32] or [64I/64I] | | | | |
| Outcome Cohort | n | events | $X^2$ | p | RH | n | events | $X^2$ | p | RH | $X^2$ | p | RH | n | events | $X^2$ | p | RH |
| AIDS-1992 | | | | | | | | | | | | | | | | | | |
| MACS | 356 | 178 | 1.91 | 0.16 | 0.79 | 331 | 215 | 3.29 | 0.07 | 0.70 | 2.71 | 0.10 | 0.73 | 339 | 222 | 5.37 | 0.02* | 0.72 |
| MHCS | 172 | 118 | 7.25 | 0.007** | 0.46 | 159 | 110 | 1.67 | 0.20 | 0.69 | 7.67 | 0.006** | 0.69 | 162 | 112 | 7.51 | 0.006* | 0.54 |
| SFCC | 76 | 47 | 0.37 | 0.54 | 0.79 | 72 | 46 | 5.39 | 0.02* | 0.59 | 0.44 | 0.44 | 0.72 | 76 | 47 | 5.23 | 0.2* | 0.48 |
| All | 612 | 394 | 6.10 | 0.01** | 0.71 | 570 | 372 | 10.82 | 0.001*** | 0.61 | 8.31 | 0.004** | 0.65 | 585 | 382 | 16.69 | $4.4\text{–}10^{-5}$**** | 0.63 |
| AIDS-1987 | | | | | | | | | | | | | | | | | | |
| MACS | 359 | 165 | 0.57 | 0.21 | 0.79 | 334 | 173 | 2.85 | 0.09 | 0.68 | 1.86 | 0.17 | 0.68 | 342 | 178 | 4.29 | 0.04* | 0.71 |
| MHCS | 172 | 83 | 1.76 | 0.18 | 0.65 | 159 | 77 | 0.95 | 0.33 | 0.70 | 3.18 | 0.07 | 0.51 | 162 | 79 | 2.69 | 0.10 | 0.64 |
| SFCC | 76 | 39 | 0.04 | 0.84 | 1.08 | 72 | 38 | 2.32 | 0.13 | 0.46 | 0.03 | 0.85 | 1.08 | 76 | 39 | 1.18 | 0.27 | 0.69 |
| All | 615 | 287 | 1.49 | 0.22 | 0.83 | 573 | 288 | 7.25 | 0.007* | 0.62 | 3.01 | 0.08 | 0.75 | 588 | 296 | 7.98 | 0.005** | 0.70 |
| Death | | | | | | | | | | | | | | | | | | |
| MACS | 359 | 142 | 4.61 | 0.03* | 0.61 | 334 | 136 | 2.23 | 0.13 | 0.69 | 6.01 | 0.01** | 0.53 | 344 | 140 | 7.09 | 0.008** | 0.61 |
| MHCS | 172 | 66 | 0.95 | 0.32 | 0.71 | 159 | 61 | 3.37 | 0.07 | 0.38 | 2.45 | 0.12 | 0.52 | 162 | 63 | 3.95 | 0.05* | 0.53 |
| SFCC | 76 | 23 | 0.04 | 0.84 | 1.12 | 72 | 23 | 1.09 | 0.30 | 0.50 | 0.17 | 0.68 | 1.27 | 76 | 23 | 0.82 | 0.48 | 0.72 |
| All | 615 | 231 | 3.10 | 0.08 | 0.73 | 573 | 220 | 7.92 | 0.005* | 0.55 | 5.71 | 0.02* | 0.61 | 588 | 226 | 11.24 | 0.0008*** | 0.60 |

What is claimed is:

1. An isolated nucleic acid molecule encoding CCR2-64I having the sequence of SEQ ID NO: 20.

2. An expression vector including the nucleic acid of claim 1.

3. The vector of claim 2, wherein the vector is a plasmid.

4. The vector of claim 2, wherein the vector is a viral vector.

5. A host cell containing the vector of claim 2.

6. The host cell of claim 5, wherein the cell is prokaryotic.

7. The host cell of claim 5, wherein the cell is eukaryotic.

8. An isolated nucleic acid molecule selected from the group consisting of:

a) SEQ ID NO: 19;

b) SEQ ID NO: 19, wherein T can also be U;

c) nucleic acid molecules that are fully complementary to a) or b); and d) fragments of a) or b) that are at least 15 bases in length and comprise nucleotides 190 to 192 of SEQ ID NO: 19 that encode isoleucine at position 64 of SEQ ID NO: 20.

9. An expression vector including an isolated nucleic acid molecule selected from the group consisting of:

a) SEQ ID NO: 19 and b) SEQ ID NO: 19, wherein T can also be U.

* * * * *

SEQUENCE LISTING

```
<160> NUMBER OF SEQ ID NOS:  20

<210> SEQ ID NO 1
<211> LENGTH: 1083
<212> TYPE: DNA
<213> ORGANISM: Homo sapiens
<220> FEATURE:
<221> NAME/KEY: CDS
<222> LOCATION: (1)...(1080)

<400> SEQUENCE: 1

atg ctg tcc aca tct cgt tct cgg ttt atc aga aat acc aac gag agc       48
Met Leu Ser Thr Ser Arg Ser Arg Phe Ile Arg Asn Thr Asn Glu Ser
  1               5                  10                  15

ggt gaa gaa gtc acc acc ttt ttt gat tat gat tac ggt gct ccc tgt       96
Gly Glu Glu Val Thr Thr Phe Phe Asp Tyr Asp Tyr Gly Ala Pro Cys
             20                  25                  30

cat aaa ttt gac gtg aag caa att ggg gcc caa ctc ctg cct ccg ctc      144
His Lys Phe Asp Val Lys Gln Ile Gly Ala Gln Leu Leu Pro Pro Leu
         35                  40                  45

tac tcg ctg gtg ttc atc ttt ggt ttt gtg ggc aac atg ctg gtc gtc      192
Tyr Ser Leu Val Phe Ile Phe Gly Phe Val Gly Asn Met Leu Val Val
     50                  55                  60

ctc atc tta ata aac tgc aaa aag ctg aag tgc ttg act gac att tac      240
Leu Ile Leu Ile Asn Cys Lys Lys Leu Lys Cys Leu Thr Asp Ile Tyr
 65                  70                  75                  80

ctg ctc aac ctg gcc atc tct gat ctg ctt ttt ctt att act ctc cca      288
Leu Leu Asn Leu Ala Ile Ser Asp Leu Leu Phe Leu Ile Thr Leu Pro
                 85                  90                  95

ttg tgg gct cac tct gct gca aat gag tgg gtc ttt ggg aat gca atg      336
Leu Trp Ala His Ser Ala Ala Asn Glu Trp Val Phe Gly Asn Ala Met
            100                 105                 110

tgc aaa tta ttc aca ggg ctg tat cac atc ggt tat ttt ggc gga atc      384
Cys Lys Leu Phe Thr Gly Leu Tyr His Ile Gly Tyr Phe Gly Gly Ile
        115                 120                 125

ttc ttc atc atc ctc ctg aca atc gat aga tac ctg gct att gtc cat      432
Phe Phe Ile Ile Leu Leu Thr Ile Asp Arg Tyr Leu Ala Ile Val His
    130                 135                 140

gct gtg ttt gct tta aaa gcc agg acg gtc acc ttt ggg gtg gtg aca      480
Ala Val Phe Ala Leu Lys Ala Arg Thr Val Thr Phe Gly Val Val Thr
145                 150                 155                 160

agt gtg atc acc tgg ttg gtg gct gtg ttt gct tct gtc cca gga atc      528
Ser Val Ile Thr Trp Leu Val Ala Val Phe Ala Ser Val Pro Gly Ile
                165                 170                 175

atc ttt act aaa tgc cag aaa gaa gat tct gtt tat gtc tgt ggc cct      576
Ile Phe Thr Lys Cys Gln Lys Glu Asp Ser Val Tyr Val Cys Gly Pro
            180                 185                 190

tat ttt cca cga gga tgg aat aat ttc cac aca ata atg agg aac att      624
Tyr Phe Pro Arg Gly Trp Asn Asn Phe His Thr Ile Met Arg Asn Ile
        195                 200                 205

ttg ggg ctg gtc ctg ccg ctg ctc atc atg gtc atc tgc tac tcg gga      672
Leu Gly Leu Val Leu Pro Leu Leu Ile Met Val Ile Cys Tyr Ser Gly
    210                 215                 220

atc ctg aaa acc ctg ctt cgg tgt cga aac gag aag aag agg cat agg      720
Ile Leu Lys Thr Leu Leu Arg Cys Arg Asn Glu Lys Lys Arg His Arg
225                 230                 235                 240

gca gtg aga gtc atc ttc acc atc atg att gtt tac ttt ctc ttc tgg      768
Ala Val Arg Val Ile Phe Thr Ile Met Ile Val Tyr Phe Leu Phe Trp
                245                 250                 255
```

-continued

```
act ccc tat aat att gtc att ctc ctg aac acc ttc cag gaa ttc ttc      816
Thr Pro Tyr Asn Ile Val Ile Leu Leu Asn Thr Phe Gln Glu Phe Phe
            260                 265                 270

ggc ctg agt aac tgt gaa agc acc agt caa ctg gac caa gcc acg cag      864
Gly Leu Ser Asn Cys Glu Ser Thr Ser Gln Leu Asp Gln Ala Thr Gln
        275                 280                 285

gtg aca gag act ctt ggg atg act cac tgc tgc atc aat ccc atc atc      912
Val Thr Glu Thr Leu Gly Met Thr His Cys Cys Ile Asn Pro Ile Ile
    290                 295                 300

tat gcc ttc gtt ggg gag aag ttc aga agg tat ctc tcg gtg ttc ttc      960
Tyr Ala Phe Val Gly Glu Lys Phe Arg Arg Tyr Leu Ser Val Phe Phe
305                 310                 315                 320

cga aag cac atc acc aag cgc ttc tgc aaa caa tgt cca gtt ttc tac     1008
Arg Lys His Ile Thr Lys Arg Phe Cys Lys Gln Cys Pro Val Phe Tyr
                325                 330                 335

agg gag aca gtg gat gga gtg act tca aca aac acg cct tcc act ggg     1056
Arg Glu Thr Val Asp Gly Val Thr Ser Thr Asn Thr Pro Ser Thr Gly
            340                 345                 350

gag cag gaa gtc tcg gct ggt tta taa                                 1083
Glu Gln Glu Val Ser Ala Gly Leu
        355                 360


<210> SEQ ID NO 2
<211> LENGTH: 360
<212> TYPE: PRT
<213> ORGANISM: Homo sapiens

<400> SEQUENCE: 2

Met Leu Ser Thr Ser Arg Ser Arg Phe Ile Arg Asn Thr Asn Glu Ser
  1               5                  10                  15

Gly Glu Glu Val Thr Thr Phe Phe Asp Tyr Asp Tyr Gly Ala Pro Cys
             20                  25                  30

His Lys Phe Asp Val Lys Gln Ile Gly Ala Gln Leu Leu Pro Pro Leu
         35                  40                  45

Tyr Ser Leu Val Phe Ile Phe Gly Phe Val Gly Asn Met Leu Val Val
     50                  55                  60

Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Leu Phe Leu Ile Thr Leu Pro
                 85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
```

-continued

```
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360


<210> SEQ ID NO 3
<211> LENGTH: 20
<212> TYPE: DNA
<213> ORGANISM: Homo sapiens

<400> SEQUENCE: 3

atgctgtcca catctcgttc                                                20


<210> SEQ ID NO 4
<211> LENGTH: 20
<212> TYPE: DNA
<213> ORGANISM: Homo sapiens

<400> SEQUENCE: 4

cccaaagacc cactcatttg                                                20


<210> SEQ ID NO 5
<211> LENGTH: 20
<212> TYPE: DNA
<213> ORGANISM: Homo sapiens

<400> SEQUENCE: 5

attactctcc cattgtgggc                                                20


<210> SEQ ID NO 6
<211> LENGTH: 21
<212> TYPE: DNA
<213> ORGANISM: Homo sapiens

<400> SEQUENCE: 6

ggaaattatt ccatcctcgt g                                              21


<210> SEQ ID NO 7
<211> LENGTH: 20
<212> TYPE: DNA
<213> ORGANISM: Homo sapiens

<400> SEQUENCE: 7

ttctgtttat gtctgtggcc                                                20


<210> SEQ ID NO 8
<211> LENGTH: 20
```

<212> TYPE: DNA
<213> ORGANISM: Homo sapiens

<400> SEQUENCE: 8
gattgatgca gcagtgagtc 20

<210> SEQ ID NO 9
<211> LENGTH: 20
<212> TYPE: DNA
<213> ORGANISM: Homo sapiens

<400> SEQUENCE: 9
ccaagccacg caggtgacag 20

<210> SEQ ID NO 10
<211> LENGTH: 20
<212> TYPE: DNA
<213> ORGANISM: Homo sapiens

<400> SEQUENCE: 10
ttataaacca gccgagactt 20

<210> SEQ ID NO 11
<211> LENGTH: 18
<212> TYPE: DNA
<213> ORGANISM: Homo sapiens

<400> SEQUENCE: 11
ttgtgggcaa catgatgg 18

<210> SEQ ID NO 12
<211> LENGTH: 20
<212> TYPE: DNA
<213> ORGANISM: Homo sapiens

<400> SEQUENCE: 12
gagcccacaa tgggagagta 20

<210> SEQ ID NO 13
<211> LENGTH: 83
<212> TYPE: PRT
<213> ORGANISM: Homo sapiens

<400> SEQUENCE: 13

Met Leu Ser Thr Ser Arg Ser Arg Phe Ile Arg Asn Thr Asn Glu Ser
1 5 10 15

Gly Glu Glu Val Thr Thr Phe Phe Asp Tyr Asp Tyr Gly Ala Pro Cys
20 25 30

His Lys Phe Asp Val Lys Gln Ile Gly Ala Gln Leu Leu Pro Pro Leu
35 40 45

Tyr Ser Leu Val Phe Ile Phe Gly Phe Val Gly Asn Met Leu Val Val
50 55 60

Leu Ile Leu Ile Asn Cys Lys Lys Leu Lys Cys Leu Thr Asp Ile Tyr
65 70 75 80

Leu Leu Asn

<210> SEQ ID NO 14
<211> LENGTH: 26
<212> TYPE: PRT
<213> ORGANISM: Homo sapiens

<400> SEQUENCE: 14

```
Met Asp Tyr Gln Val Ser Ser Pro Ile Tyr Asp Ile Asn Tyr Thr Ser
 1               5                  10                  15

Glu Gln Ile Asn Ala Arg Ile Arg Ser Met
            20                  25


<210> SEQ ID NO 15
<211> LENGTH: 39
<212> TYPE: PRT
<213> ORGANISM: Homo sapiens

<400> SEQUENCE: 15

Met Glu Thr Pro Asn Thr Thr Glu Asp Tyr Asp Thr Tyr Glu Ile Asn
 1               5                  10                  15

Gly Asp Ala Thr Gln Val Asn Glu Arg Ala Phe Val Ile Leu Ile Val
            20                  25                  30

Val Gln Tyr Arg Asn Met Ser
        35


<210> SEQ ID NO 16
<211> LENGTH: 43
<212> TYPE: PRT
<213> ORGANISM: Homo sapiens

<400> SEQUENCE: 16

Met Thr Thr Ser Leu Asp Thr Val Glu Thr Phe Gly Ser Tyr Tyr Asn
 1               5                  10                  15

Val Leu Leu Glu Ala Thr Arg Ala Leu Met Phe Val Thr Val Leu Leu
            20                  25                  30

Val Val Met Lys Tyr Arg Arg Arg Ile Met Asn
        35                  40


<210> SEQ ID NO 17
<211> LENGTH: 50
<212> TYPE: PRT
<213> ORGANISM: Homo sapiens

<400> SEQUENCE: 17

Met Asn Pro Thr Asp Ile Ala Asp Thr Leu Asp Glu Ser Ile Tyr Ser
 1               5                  10                  15

Asn Tyr Tyr Leu Tyr Glu Ser Ile Pro Lys Pro Thr Glu Gly Ile Ala
            20                  25                  30

Phe Glu Leu Phe Val Leu Leu Ser Val Val Phe Lys Tyr Arg Arg Ser
        35                  40                  45

Met Val
    50


<210> SEQ ID NO 18
<211> LENGTH: 56
<212> TYPE: PRT
<213> ORGANISM: Homo sapiens

<400> SEQUENCE: 18

Met Glu Gly Ile Ser Tyr Thr Ser Asp Asn Tyr Ser Met Gly Ser Gly
 1               5                  10                  15

Asp Tyr Asp Ser Met Lys Glu Pro Phe Arg Glu Glu Asn Ala Asn Phe
            20                  25                  30

Asn Lys Ile Phe Thr Ile Ile Ile Leu Thr Ile Gly Ile Val Met Gly
        35                  40                  45

Tyr Gln Arg Ser Met Lys Arg His
```

50 55

<210> SEQ ID NO 19
<211> LENGTH: 1083
<212> TYPE: DNA
<213> ORGANISM: Homo sapiens

<400> SEQUENCE: 19

```
atgctgtcca catctcgttc tcggtttatc agaaatacca acgagagcgg tgaagaagtc     60

accacctttt ttgattatga ttacggtgct ccctgtcata aatttgacgt gaagcaaatt    120

ggggcccaac tcctgcctcc gctctactcg ctggtgttca tctttggttt tgtgggcaac    180

atgctggtca tcctcatctt aataaactgc aaaaagctga agtgcttgac tgacatttac    240

ctgctcaacc tggccatctc tgatctgctt tttcttatta ctctcccatt gtgggctcac    300

tctgctgcaa atgagtgggt ctttgggaat gcaatgtgca aattattcac agggctgtat    360

cacatcggtt attttggcgg aatcttcttc atcatcctcc tgacaatcga tagatacctg    420

gctattgtcc atgctgtgtt tgctttaaaa gccaggacgg tcacctttgg ggtggtgaca    480

agtgtgatca cctggttggt ggctgtgttt gcttctgtcc caggaatcat ctttactaaa    540

tgccagaaag aagattctgt ttatgtctgt ggcccttatt ttccacgagg atggaataat    600

ttccacacaa taatgaggaa cattttgggg ctggtcctgc cgctgctcat catggtcatc    660

tgctactcgg gaatcctgaa aaccctgctt cggtgtcgaa acgagaagaa gaggcatagg    720

gcagtgagag tcatcttcac catcatgatt gtttactttc tcttctggac tccctataat    780

attgtcattc tcctgaacac cttccaggaa ttcttcggcc tgagtaactg tgaaagcacc    840

agtcaactgg accaagccac gcaggtgaca gagactcttg ggatgactca ctgctgcatc    900

aatcccatca tctatgcctt cgttggggag aagttcagaa ggtatctctc ggtgttcttc    960

cgaaagcaca tcaccaagcg cttctgcaaa caatgtccag ttttctacag ggagacagtg   1020

gatggagtga cttcaacaaa cacgccttcc actggggagc aggaagtctc ggctggttta   1080

taa                                                                 1083
```

<210> SEQ ID NO 20
<211> LENGTH: 360
<212> TYPE: PRT
<213> ORGANISM: Homo sapiens

<400> SEQUENCE: 20

```
Met Leu Ser Thr Ser Arg Ser Arg Phe Ile Arg Asn Thr Asn Glu Ser
 1               5                  10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Ile
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125
```

-continued

```
Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360
```